US008802121B2

(12) United States Patent
Kurdyumov et al.

(10) Patent No.: US 8,802,121 B2
(45) Date of Patent: Aug. 12, 2014

(54) SILANE-FUNCTIONALIZED HYDROPHOBIC α(1→4)GLUCOPYRANOSE POLYMERS AND POLYMERIC MATRICES FOR IMPLANTATION OR INJECTION

(75) Inventors: Aleksey V. Kurdyumov, Maplewood, MN (US); Nathan A. Lockwood, Minneapolis, MN (US); Joram Slager, St. Louis Park, MN (US); Dale G. Swan, St. Louis Park, MN (US); Robert Hergenrother, Eden Prairie, MN (US)

(73) Assignee: Surmodics, Inc., Eden Prairie, MN (US)

(*) Notice: Subject to any disclaimer, the term of this patent is extended or adjusted under 35 U.S.C. 154(b) by 802 days.

(21) Appl. No.: 12/792,365

(22) Filed: Jun. 2, 2010

(65) Prior Publication Data
US 2010/0303879 A1    Dec. 2, 2010

Related U.S. Application Data

(60) Provisional application No. 61/217,625, filed on Jun. 2, 2009.

(51) Int. Cl.
| A61F 13/00 | (2006.01) |
| B32B 9/04 | (2006.01) |
| B32B 9/06 | (2006.01) |
| B32B 15/04 | (2006.01) |
| C08G 63/91 | (2006.01) |
| C08G 65/32 | (2006.01) |
| C08L 67/00 | (2006.01) |
| C08L 71/00 | (2006.01) |

(52) U.S. Cl.
USPC ............ 424/422; 428/447; 428/452; 525/410

(58) Field of Classification Search
None
See application file for complete search history.

(56) References Cited

U.S. PATENT DOCUMENTS

| 4,011,392 | A | 3/1977 | Rudolph et al. |
| 5,459,258 | A | 10/1995 | Merrill et al. |
| 5,470,581 | A | 11/1995 | Grillo et al. |
| 5,869,647 | A | 2/1999 | Narayan et al. |
| 6,007,614 | A | 12/1999 | Billmers et al. |
| 6,528,642 | B1 | 3/2003 | Duval et al. |
| 6,562,961 | B1 | 5/2003 | Seeger et al. |
| 7,438,722 | B1* | 10/2008 | Hossainy ..................... 623/1.42 |
| 7,919,111 | B2 | 4/2011 | Chudzik et al. |
| 2002/0058763 | A1 | 5/2002 | Duval |
| 2002/0123624 | A1 | 9/2002 | Qiao et al. |
| 2003/0215649 | A1 | 11/2003 | Jelle |
| 2004/0037886 | A1 | 2/2004 | Hsu |
| 2004/0208985 | A1 | 10/2004 | Rowan et al. |
| 2005/0019371 | A1 | 1/2005 | Anderson et al. |
| 2005/0255142 | A1 | 11/2005 | Chudzik et al. |
| 2006/0249705 | A1 | 11/2006 | Wang et al. |
| 2007/0065481 | A1 | 3/2007 | Chudzik et al. |
| 2007/0087025 | A1 | 4/2007 | Fitzhugh et al. |
| 2007/0218102 | A1 | 9/2007 | Chudzik et al. |
| 2007/0224247 | A1 | 9/2007 | Chudzik et al. |
| 2007/0260054 | A1 | 11/2007 | Chudzik |
| 2008/0145786 | A1* | 6/2008 | Kim et al. .................. 430/287.1 |
| 2009/0124798 | A1* | 5/2009 | Okamoto et al. ............... 536/56 |
| 2010/0093662 | A1 | 4/2010 | Defaye et al. |
| 2010/0099861 | A1 | 4/2010 | Okamoto et al. |
| 2010/0303879 | A1 | 12/2010 | Kurdyumov et al. |
| 2010/0316687 | A1 | 12/2010 | Swan et al. |
| 2011/0076314 | A1 | 3/2011 | Kurdyumov |
| 2011/0076337 | A1 | 3/2011 | Slager et al. |
| 2011/0159067 | A1 | 6/2011 | Rolfes Meyering |
| 2011/0159101 | A1 | 6/2011 | Kurdyumov et al. |

FOREIGN PATENT DOCUMENTS

| EP | 0 405 917 | | 1/1991 |
| EP | 644204 | A1 * | 3/1995 |
| JP | 2001/321094 | | 3/2001 |
| WO | 02/094224 | | 11/2002 |
| WO | WO 2007129659 | A1 * | 11/2007 |

OTHER PUBLICATIONS

PCT Search Report for International Application No. PCT/US2010/037027; mailed on Sep. 2, 2010.
Péan, et al. (1999) *Why Does PEG 400 Co-Encapsulation Improve NGF Stability and Release from PLGA Biodegradable Microspheres?* Pharmaceutical Research 16: 1294-1299.
Varela, et al., (2005) *Evaluation of biochemical analytes in vitreous humor collected after death in West Indian manatees*, JAVMA 226: 88-92.
Chen, et al., (1995) *Enzymatic and chemoenzymatic approaches to synthesis of sugar-based polymer and hydrogels*, Carbohydrate Polymers 28: 15-21.
van Veen, et al. (2005) *The Effect of powder blend and tablet structure on drug release mechanisms of hydrophobic starch acetate matrix tablets*, European Journal of Pharmaceutics and Biopharmaceutics 61: 149-157.
Tarvainen, et al. (2004) *Aqueous starch acetate dispersion as a novel coating material for controlled release products*, Journal of Controlled Release 96: 179-191.
Magdassi, et al. (2001) *Interfacial Properties of Hydrophobically Modified Biomolecules: Fundamental Aspects and Applications*, J. Dispersion Science and Technology 22: 313-322.

(Continued)

*Primary Examiner* — Juliet Switzer
*Assistant Examiner* — Caralynne Helm
(74) *Attorney, Agent, or Firm* — Kagan Binder, PLLC

(57) ABSTRACT

Silane-functionalized hydrophobic α(1→4)glucopyranose polymers and polymeric matrices are described. Biodegradable matrices can be formed from hydrophobic α(1→4)glucopyranose polymers with reactive pendent silyl ether groups. Reaction of the silyl ether groups provides improved matrix formation through bonding to a device surface of a device, polymer-polymer crosslinking, or both. Biodegradable matrices can be used for the preparation of implantable and injectable medical devices, including those that release a bioactive agent.

10 Claims, 5 Drawing Sheets

(56) References Cited

OTHER PUBLICATIONS

Na, et al. (2003) *Self-assembled nanoparticles of hydrophobically-modified polysaccharide bearing vitamin H as a targeted anti-cancer drug delivery system*, European Journal of Pharmaceutical Sciences 18: 165-173.

Uekama, K. (2004) *Pharmaceutical Application of Cyclodextrins as Multi-functional Drug Carriers*, Yakugaku Zasshi 124: 909-935.

Kaur, et al. (2004) *Role of Cyclodextrins in Ophthalmics*, Current Drug Delivery. 1: 351-360.

* cited by examiner

Figure 2A
Figure 2B
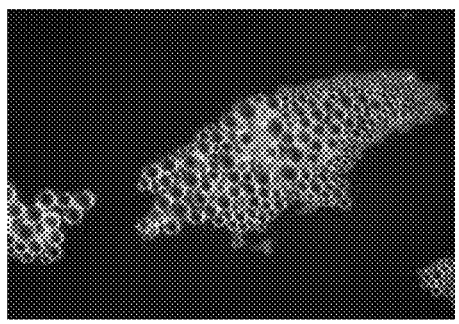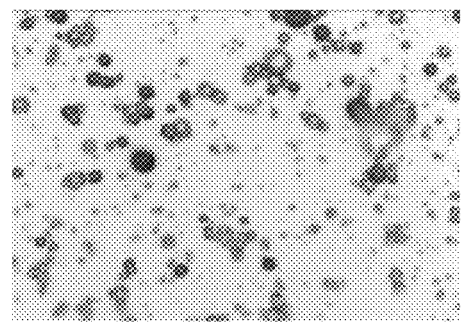

SILANE-FUNCTIONALIZED HYDROPHOBIC α(1→4)GLUCOPYRANOSE POLYMERS AND POLYMERIC MATRICES FOR IMPLANTATION OR INJECTION

PRIORITY CLAIM

This application claims the benefit of U.S. Provisional Patent Application Ser. No. 61/217,625 filed Jun. 2, 2009, entitled Silane-Functionalized Hydrophobic α(1→4)Glucopyranose Polymers and Polymeric Matrices for Implantation or Injection, the disclosure of which is incorporated herein by reference.

TECHNICAL FIELD

The present invention relates to hydrophobic derivatives of polysaccharides having pendent silane-containing groups, and articles including these derivatives for use within the body.

BACKGROUND

Biodegradable polymers have been used to prepare biodegradable polymeric matrices, and these matrices can be associated with, or formed into, implantable medical devices. For example, biodegradable polymers can be used to make a thin coating on the surface of a device. Biodegradable polymers having thermoplastic properties can even be molded or formed into a shape to provide an implantable device having useful structural properties. Use of biodegradable matrices can be advantageous because the polymeric matrix becomes totally degraded in the body and there is no need to perform an explantation procedure.

Implantable articles having biodegradable polymeric matrices can also be used to modulate the delivery of drugs to a patient at the site of implantation. Drug-releasing biodegradable matrices can also be in the form of a coating on a device or in the form of an implantable or injectable article that is formed primarily of the biodegradable polymer. Drug contained within the biodegradable matrix can be generally released or eluted from the matrix after the article has been introduced into the body.

The present invention is directed to hydrophobic derivatives of natural biodegradable polysaccharides having pendent silyl ether groups and biodegradable polymeric matrices formed from these polymers. The polymeric matrices can be formed into or associated with an implantable or injectable medical article The polymers and matrices of the invention have been found to provide one or more of the following: improvements for formation of a polymeric matrix in a desired form, such as a medical device coating, a microparticle, or a medical implant; improvements in biocompatibility, and improvements in degradation properties of a matrix formed from these polymers.

SUMMARY OF THE INVENTION

Generally, the present invention relates to hydrophobic derivatives of natural biodegradable polysaccharides having pendent silyl ether groups. The invention also relates to polymeric matrices formed from these polymers, articles including these polymeric matrices, and methods for using these matrices.

In one aspect, the invention provides a silyl ether-modified hydrophobic α(1→4)glucopyranose polymer. Generally, the polymer includes a poly-α(1→4)glucopyranose portion and a plurality of hydrophobic groups pendent from the poly-α(1→4)glucopyranose portion. The hydrophobic groups include a hydrocarbon segment including two or more carbon atoms. The polymer also includes one or more silyl ether groups pendent from the poly-α(1→4)glucopyranose portion.

The silyl ether groups can undergo reaction to promote matrix formation. For example, the silyl ether groups can hydrolyze upon contact with water and bond to a target component. Exemplary targets include a material on the surface of a device, or a silyl ether group from another silyl ether-modified hydrophobic α(1→4)glucopyranose polymer such as to provide polymer-polymer crosslinking.

The reactive silanol groups promote improved matrix formation though the covalent bonding. In some aspects the improved matrix formation is caused by crosslinking between the α(1→4)glucopyranose polymer portions via siloxane groups. Such crosslinking can provide an implantable article having a polymeric matrix, such as a microparticle, with a higher degree of durability.

In some cases, the silyl ether groups are reacted to covalently bond the α(1→4)glucopyranose polymer to a target surface. Bonding to a material on the surface of a device can result in the formation of a layer of coated hydrophobic α(1→4)glucopyranose polymer on the device surface via a siloxy linkage. Such bonding can provide a more stable coating on the surface of a device by improved attachment of polymeric material.

The article including the polymeric matrix can be in various forms, such as microparticles, a coated layer on a device surface, a freestanding film, or a three-dimensional implant. Therefore, in another aspect, the invention provides an implantable or injectable biomedical article, the article comprising a polymeric matrix comprising hydrophobic α(1→4) glucopyranose polymers having pendent reacted silyl ether groups.

The article having a polymeric matrix formed from silyl ether-modified hydrophobic α(1→4)glucopyranose polymer can be introduced into the body. After a period of time, the polymeric matrix can degrade. In one mode of degradation, the linkages between the pendent hydrophobic groups and/or pendent silyl ether groups hydrolyze, causing the α(1→4) glucopyranose portion to become less hydrophobic and susceptible to dissolution and enzymatic degradation by body amylases. The hydrophobic polysaccharides can be degraded into natural materials, which provide advantages for compatibility of implantable articles. Degradation of the matrix can result in the release of, for example, naturally occurring mono- or disaccharides, such as glucose, which are common serum components.

It has also been found that the silyl ether groups impart properties to the hydrophobic polysaccharide that render it particularly useful for forming improved compositions. These compositions, in turn, are useful for forming polymeric matrix-containing articles that can be implanted or injected into the body.

In some aspects, the silyl ether-modified hydrophobic α(1→4)glucopyranose polymer is present in a composition in the form of a emulsion. The emulsion can facilitate the formation of the polymeric matrix-containing articles, such as coatings and microparticles. In some specific aspects, the invention provides a highly stable emulsion that includes the silyl ether-modified hydrophobic α(1→4)glucopyranose polymer and an emulsion stabilizing component comprising an arylboronic acid. In some aspects, the emulsion-stabilizing component comprises a halogenated arylboronic acid. Phase separation of the emulsion does not easily occur, which facilitates the preparation of articles having a matrix including the hydrophobic α(1→4)glucopyranose polymer.

In some aspects, the polymeric matrix including the silyl ether-modified hydrophobic α(1→4)glucopyranose polymer is associated with an implantable or injectable medical article, and the article is capable of releasing a bioactive agent in a subject. The silyl ether-modified hydrophobic α(1→4) glucopyranose polymer can be used in association with the article to modulate release of the bioactive agent. In some aspects, the silyl ether-modified hydrophobic α(1→4)glucopyranose polymer is used as a control-release polymeric layer in association with a second polymeric matrix that includes and is able to release the bioactive agent. The silyl ether-modified hydrophobic α(1→4)glucopyranose polymer (e.g., in the form of a polymeric tie layer) can also facilitate the immobilization of a second polymeric matrix that includes and is able to release the bioactive agent.

BRIEF DESCRIPTION OF THE DRAWINGS

FIG. 2A is a micrograph of microparticles formed using the silyl ether-modified hydrophobic α(1→4)glucopyranose polymer, and FIG. 2B a micrograph of the material after a drop of DCM was applied to dissolve the microparticles.

DETAILED DESCRIPTION

Figure 1A:
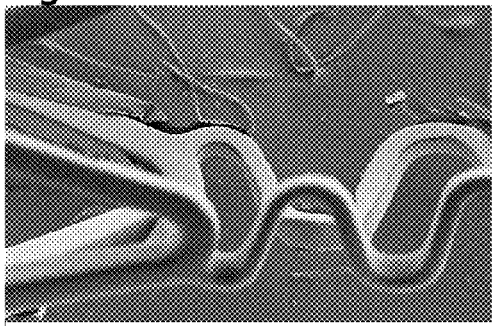
FIGS. 1A and 1B are micrographs of stents having a hydrophobic polymeric coating without a tie layer, the micrographs taken after balloon expansion of the stents.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The invention is generally directed to silyl ether-modified hydrophobic α(1→4)glucopyranose polymers, compositions including these polymers, and articles that are formed using these polymers, as well as uses of these articles, such as localized drug delivery.

As a general matter, the silyl ether-modified hydrophobic α(1→4)glucopyranose polymer includes at least three portions. The first portion is a α(1→4)glucopyranose polymeric backbone. The second portion is a hydrophobic portion including hydrophobic groups that are pendent from the α(1→4)glucopyranose polymeric backbone. The plurality of pendent groups is collectively referred to as the "hydrophobic portion" of the hydrophobic derivative. The third portion includes one or more silyl ether groups pendent from the poly-α(1→4)glucopyranose portion.

Overall, the silyl ether-modified hydrophobic α(1→4)glucopyranose polymer displays hydrophobic properties. The polymer has one or more functional silyl ether groups that can be reacted to form a polymeric matrix, or to attach the hydrophobic α(1→4)glucopyranose polymers to a surface of a device.

Aspects of the invention embrace polymers that include a hydrophobic α(1→4)glucopyranose polymer with one or more pendent group(s) including a silane atom, as well as matrices formed from these polymers. In other words, the invention includes hydrophobic α(1→4)glucopyranose polymers having a pendent group with an unreacted (latent) silyl ether group, as well as polymers wherein the silyl ether group has been reacted to provide a polymeric matrix form, wherein the silane atom remains as a part of the formed matrix.

An α(1→4)glucopyranose polymer, which forms the poly-α(1→4)glucopyranose portion of the silyl ether-modified hydrophobic α(1→4)glucopyranose polymer, includes repeating α-D-glucopyranose ($Glc_p$) monomers having α(1→4) linkages. A portion (three monomeric units) of an α(1→4) glucopyranose polymer is shown below:

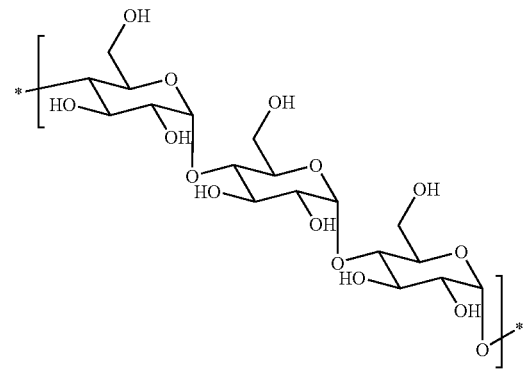

As starting material for the preparation of the silyl ether-modified hydrophobic α(1→4)glucopyranose polymer, one can use exemplary α(1→4)glucopyranose polymers, such as maltodextrin, amylose, cyclodextrin, and polyalditol (polyalditol is available from GPC (Muscatine, Iowa) under the tradename Innovatol™ PD60, and has <1% reducing sugars). Maltodextrins generally refer to those polymer preparations having a lower molecular weight than amylose preparations. Cyclodextrins are low molecular weight cyclic α(1→4)glucopyranose polymers.

Maltodextrin is typically generated by hydrolyzing a starch slurry with a heat-stable α-amylase at temperatures at 85-90° C. until the desired degree of hydrolysis is reached and then inactivating the α-amylase by a second heat treatment. The maltodextrin can be purified by filtration and then spray dried to a final product. Maltodextrins are typically characterized by their dextrose equivalent (DE) value, which is related to the degree of hydrolysis defined as: DE=MW dextrose/number-averaged MW starch hydrolysate×100. Generally, maltodextrins are considered to have molecular weights that are less than amylose molecules.

A starch preparation that has been totally hydrolyzed to dextrose (glucose) has a DE of 100, whereas starch has a DE of about zero. A DE of greater than 0 but less than 100 characterizes the mean-average molecular weight of a starch hydrolysate, and maltodextrins are considered to have a DE of less than 20. Maltodextrins of various molecular weights are commercially available.

As used herein, "amylose" or "amylose polymer" refers to a linear polymer having repeating glucopyranose units that are joined by α-1,4 linkages. Some amylose polymers can have a very small amount of branching via α-1,6 linkages (about less than 0.5% of the linkages) but still demonstrate the same physical properties as linear (unbranched) amylose polymers do. Generally amylose polymers derived from plant sources have molecular weights of about $1\times10^6$ Da or less. Amylopectin, comparatively, is a branched polymer having repeating glucopyranose units that are joined by α-1,4 linkages to form linear portions and the linear portions are linked together via α-1,6 linkages. The branch point linkages are generally greater than 1% of the total linkages and typically 4%-5% of the total linkages. Generally amylopectin derived from plant sources have molecular weights of $1\times10^7$ Da or greater.

Exemplary maltodextrin and amylose polymers have molecular weights ranging from about 500 Da to about 500,000 Da, about 1000 Da to about 300,000 Da, and about 5000 Da to about 100,000 Da, and generally greater than 3, 5, or about 10 repeating glucopyranose units.

Maltodextrin and amylose polymers of various molecular weights are commercially available from a number of different sources. For example, Glucidex™ 6 (ave. molecular weight ~95,000 Da) and Glucidex™ 2 (ave. molecular weight ~300,000 Da) are available from Rouquette (France); and MALTRIN™ maltodextrins of various molecular weights, including molecular weights from about 12,000 Da to 15,000 Da are available from GPC (Muscatine, Iowa).

The decision of using amylose of a particular size range may depend on factors such as the physical characteristics of the composition, the desired rate of degradation of the matrix formed from the polysaccharide, and the presence of other optional components in the matrix, such as bioactive agents.

Refinement of the molecular weight of a polymer preparation (such as the α(1→4)glucopyranose polymer starting material) can be carried out using diafiltration. Diafiltration of polysaccharides such as maltodextrin can be carried out using ultrafiltration membranes with different pore sizes. As an example, use of one or more cassettes with molecular weight cut-off membranes in the range of about 1K to about 500 K can be used in a diafiltration process to provide polysaccharide preparations with average molecular weights in the range of less than 500 kDa, in the range of about 100 kDa to about 500 kDa, in the range of about 5 kDa to about 30 kDa, in the range of about 30 kDa to about 100 kDa, in the range of about 10 kDa to about 30 kDa, or in the range of about 1 kDa to about 10 kDa.

The polymers as discussed herein can be described in terms of molecular weight. "Molecular weight," as used herein, more specifically refers to the "weight average molecular weight" or $M_w$, which is an absolute method of measuring molecular weight and is particularly useful for measuring the molecular weight of a polymer (preparation). Polymer preparations typically include polymers that individually have minor variations in molecular weight. In some cases, the polymers have a relatively higher molecular weight (e.g., versus smaller organic compounds) and such minor variations within the polymer preparation do not affect the overall properties of the polymer preparation (for example, the characteristics of an initiator polymer preparation). The weight average molecular weight ($M_w$) can be defined by the following formula:

$$M_w = \frac{\sum_i N_i M_i^2}{\sum_i N_i M_i}$$

wherein N represents the number of moles of a polymer in the sample with a mass of M, and $\Sigma_i$ is the sum of all $N_iM_i$ (species) in a preparation. The $M_w$, can be measured using common techniques, such as light scattering or ultracentrifugation. Discussion of $M_w$ and other terms used to define the molecular weight of polymer preparations can be found in, for example, Allcock, H. R. and Lampe, F. W., *Contemporary Polymer Chemistry*; pg 271 (1990).

Compounds providing hydrophobic groups and silyl ether groups can be coupled to monomeric units along the length of the α(1→4)glucopyranose polymer to provide pendent hydrophobic groups and silyl ether groups. The derivatized α(1→4)glucopyranose polymer can include: (a) a derivatized glucopyranose monomeric unit having a pendent hydrophobic and silyl ether groups, (b) a derivatized glucopyranose monomeric unit having a pendent hydrophobic group, (c) a derivatized glucopyranose monomeric unit having a pendent silyl ether group, and (d) an underivatized glucopyranose monomeric unit.

In underivatized form, the glucopyranose units of the α(1→4)glucopyranose polymers include monomeric units having ring structures with primary and secondary hydroxyl groups. In forming the silyl ether-modified hydrophobic α(1→4)glucopyranose polymer, a compound having a hydrophobic group with a hydrocarbon segment, and a compound having a silyl ether group, can be individually covalently coupled to one or more portions of an α(1→4) glucopyranose polymer. Primary and secondary hydroxyl groups can be reacted with hydroxyl reactive compounds to provide hydrophobic and silyl ether groups pendent from positions on the glucopyranose monomeric units previously corresponding to either or both primary and/or secondary hydroxyl locations. In some modes of practice, following reaction, more of the primary hydroxyl groups than secondary hydroxyl groups become derivatized with the hydrophobic and silyl ether groups.

The compounds having the hydrocarbon segment and the silyl ether group can include a group that is reactive with a hydroxyl group of the glucopyranose unit on the polymer. Examples of hydroxyl-reactive groups include acetal, carboxyl, anhydride, acid halide, silane, silazane, and the like. These groups can be used to form a hydrolytically-cleavable covalent bond, such as ester or carbonate ester, between the hydrophobic group and/or the silyl ether group and the glucopyranose unit of the polysaccharide backbone. In some aspects, the synthesized hydrophobic polysaccharide can include chemical linkages that are both enzymatically cleavable (i.e., in the polymer backbone) and non-enzymatically hydrolytically cleavable (e.g., in the linkage between either, or both, the pendent hydrophobic group and/or pendent silyl ether group).

Other cleavable chemical linkages that can be used to bond the pendent groups to the polysaccharide include peroxyester groups, disulfide groups, silyl ether, and hydrazone groups. Some chemical linkages, such as ones including urethane bonds, have a slow rate of hydrolysis. In some cases the hydroxyl reactive groups include those such as isocyanate and epoxy. These groups can be used to form a non-cleavable covalent bond between the pendent group hydrophobic group and/or silyl ether group and the polysaccharide backbone.

Optionally, the silyl ether-modified hydrophobic α(1→4) glucopyranose polymer, can be synthesized so the pendent groups are individually linked to the polysaccharide backbone via both hydrolyzable and non-hydrolyzable bonds. For example, a hydrophobic α(1→4)glucopyranose polymer is prepared by reacting a mixture of butyric acid anhydride and butyl isocyanate with maltodextrin. This yields a hydrophobic α(1→4)glucopyranose polymer with pendent butyl groups that are individually covalently bonded to the maltodextrin backbone with hydrolyzable ester linkages and non-hydrolyzable urethane linkages.

When placed in the body, the degradation of a polymeric matrix having this type of hydrophobic polysaccharide can occur by loss of the butyrate groups from hydrolysis of the ester linkages. However, a portion of the butyrate groups (the ones that are bonded via the urethane groups) are not removed from the polysaccharide backbone and therefore the polysaccharide can maintain a desired degree of hydrophobicity prior to enzymatic degradation of the polysaccharide backbone.

The hydrophobic group includes a hydrocarbon segment. The hydrocarbon segments, taken in total, can represent all or a part of the hydrophobic portion of the polymer. The hydrocarbon segment can be a linear, branched, or cyclic group containing two or more carbon atoms and two or more hydrogen atoms. A hydrocarbon segment can include saturated hydrocarbon groups or unsaturated hydrocarbon groups, and examples thereof include alkyl, alkenyl, alkynyl, cyclic alkyl, cyclic alkenyl, aromatic hydrocarbon and aralkyl groups. In some aspects, the hydrocarbon segment comprises a $C_2$-$C_{18}$-containing, a $C_2$-$C_{10}$-containing, or a $C_4$-$C_8$-containing, linear, branched, or cyclic hydrocarbon group. In some aspects the hydrocarbon segment has the formula —$(CH_n)_m$—$CH_3$, wherein m is 2 or greater, and n is independently 2 or 1. In some cases, two or more hydrocarbon segments are present in a single pendent group and are separated from each other by a non-carbon atom, or a non-carbon-containing group.

Pendent hydrophobic groups can be formed by reaction of a α(1→4)gluco-pyranose polymer with a compound having one or more hydrocarbon segments and a hydroxyl-reactive group. In some aspects this compound is derived from a natural compound. Natural compounds with hydrocarbon segments include fatty acids, fats, oils, waxes, phospholipids, prostaglandins, thromboxanes, leukotrienes, terpenes, steroids, and lipid soluble vitamins.

Exemplary natural compounds with hydrocarbon segments and reactive with hydroxyl groups include fatty acids and derivatives thereof, such as fatty acid anhydrides and fatty acid halides. Exemplary fatty acids and anhydrides include acetic, propionic, butyric, isobutyric, valeric, caproic, caprylic, capric, and lauric acids and anhydrides, respectively. Reaction of the hydroxyl group can form an ester group between the hydrocarbon segment of the compound to the monomeric unit of the α(1→4)gluco-pyranose polymer.

The hydroxyl group of a polysaccharide can also cause the ring opening of lactones to provide pendent open-chain hydroxy esters. Exemplary lactones that can be reacted with the polysaccharide include caprolactone and glycolides.

Optionally, the hydrophobic poly(α(1→4)glucopyranose) can be synthesized having pendent groups with two or more different hydrocarbon segments. For example, the hydrophobic polysaccharide can be synthesized using compounds having hydrocarbon segments with different alkyl chain lengths.

The type of hydrocarbon segment present in the pendent hydrophobic groups can influence the hydrophobic properties of the polymer. Generally, if compounds having large hydrocarbon segments are used for the synthesis of the hydrophobic polysaccharide, a smaller amount of the compound may be needed for reaction with the α(1→4)glucopyranose polymer to provide hydrophobicity. The amount of hydrophobic groups made pendent from the polymer backbone can be characterized by a degree of substitution (DS), which is defined as the average number of hydrophobic groups linked to each sugar residue. Since each glucopyranose monomer unit in the polymer has three hydroxyls available for modification, DS values range from zero to three (full substitution). For example, if a compound having a hydrocarbon segments with an alkyl chain length of $C_x$ is used to prepare a hydrophobic polysaccharide with a DS of 1, a compound having a hydrocarbon segment with an alkyl chain length of $C_{(2x)}$ is reacted in an amount to provide a hydrophobic polysaccharide with a DS of 0.5. For example, using hexanoic (i.e., an alkyl chain length of 6) anhydride a degree of substitution of the hydroxyl groups of about 0.9 or greater, such as is in the range of about 0.9-2.5, provides a hydrophobic α(1→4)glucopyranose polymer.

The degree of substitution can influence the hydrophobic character of the polysaccharide. In turn, polymeric matrices formed from silyl ether-modified hydrophobic α(1→4)glucopyranose polymers having a high weight ratio of the hydrophobic portion to the α(1→4)glucopyranose polymer (as exemplified by a high DS) are generally more hydrophobic and can be more resistant to degradation. For example, a matrix formed from silyl-ether modified maltodextrin-hexanoate DS1 may have a rate of degradation that is faster than a matrix formed from silyl-ether modified maltodextrin-hexanoate DS2.

In some modes of practice, the modification provides the polysaccharide backbone with an overall degree of substitution of about 0.16 or less, the overall degree of substitution based on the combined amount of pendent hydrophobic groups and silyl ether groups. This overall degree of substitution can allow enzymatic degradation of the polysaccharide backbone without requiring any hydrolysis to release the hydrophobic groups or silyl ether groups, and reforming of the natural hydroxyl groups.

In preparing the silyl ether-modified hydrophobic α(1→4) glucopyranose polymer any suitable synthesis procedure can be performed. Synthesis can be carried out to provide a desired number of hydrophobic groups and silyl ether groups pendent from the polysaccharide backbone. The number and/or density of the pendent groups can be controlled, for example, by controlling the relative concentration of the compound that includes the hydrophobic group to the available reactive groups (e.g., hydroxyl groups) on the polysaccharide, as well as the compound that includes the silyl ether group.

The relationship between the hydrophobic portion and the poly-α(1→4)glucopyranose portion can be expressed by the weight ratio between the two. For example, the relationship can be calculated by comparing the weight amount of the α(1→4)glucopyranose polymer to the weight amount by weight of the hydrocarbon segment of the compound reacted to provide the pendent hydrophobic groups. The total weight of the hydrocarbon segments represents the hydrophobic portion.

In some aspects, in the silyl ether-modified hydrophobic α(1→4)glucopyranose polymer, the weight ratio of the poly-α(1→4)glucopyranose portion to the hydrophobic portion is in the range of about 1.4:1 to about 1:1.77, respectively. In more specific aspects the weight ratio is in the range of about 1.13:1 to about 1:1.24, respectively.

In many aspects, on a weight basis, the combined weight of the polysaccharide portion and the hydrophobic portion (versus the pendent silyl ether groups) comprise the majority of the weight of the silyl ether-modified hydrophobic α(1→4) glucopyranose polymer.

The following general process outlined steps describing reagent types and use of reagents in suggested ranges to provide a hydrophobic α(1→4)glucopyranose. In order to provide a desired product, one of skill could modify the process by substituting the cited reagents with similar reagents, in amounts appropriate to provide a hydrophobic polysaccharide.

A first step in preparing the silyl ether-modified hydrophobic α(1→4)gluco-pyranose polymer can be carried out using a general process as follows. Maltodextrin having a starting molecular weight in the range of about 100-500 kDa is dissolved in a solvent suitable, such as dimethylsulfoxide (DMSO), in the range of about 150 mg/mL to about 250 mg/mL. A compound such as methylimidazole, is added to the maltodextrin solution in an amount in the range of about 10 to about 15 mmol/gram. A compound such as methylimidazole serves as a catalyst, as well as a base to trap free acid that is formed during the reaction. Next, a fatty acid anhydride such as hexanoic anhydride is added at a mole to weight ratio in the range of about 5 to about 15 mmol/gram. The reaction takes place at room temperature for a period of time, and then is quenched with water. The solid (hydrophobic maltodextrin) can then be collected by vacuum filtration, washed with water, and further purified by dialysis.

This provides hydrophobic maltodextrin, which can subsequently be reacted with a silyl ether-containing compound to provide the hydrophobic maltodextrin with pendent reactive silyl ether groups.

The "silyl ether group" includes a silicon atom bonded to one or more carbon-containing groups via an oxygen atom (i.e., an ether linkage). Exemplary carbon-containing groups that can form a portion of the silyl ether group include covalently bonded carbon atoms having the formula —$(CH_2)_m CH_3$, wherein m is 0 or an integer in the range of 1 to 5.

In some aspects, the silyl ether group is according to formula I:

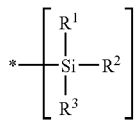

In formula I, $R^1$, $R^2$, and $R^3$ are independently selected from $R^4$ and $OR^4$, wherein $R^4$ includes a hydrocarbon group, such as a C1-C6-containing hydrocarbon group, or more specifically a linear or branched C1-C6 alkyl group, with the proviso that at least one of $R^1$, $R^2$, or $R^3$ is $OR^4$. For example, in some more specific aspects of formula I, one of $R^1$, $R^2$, or $R^3$ is $OR^4$, wherein $R^4$ is a hydrocarbon group, such as a C1-C6-containing hydrocarbon group, and the other groups that are not $OR^4$ are independently selected from $R^4$.

In other specific aspects of formula I, all of $R^1$, $R^2$, and $R^3$, are independently selected from $OR^4$, wherein $R^4$ is a C1-C6-containing hydrocarbon group.

Exemplary hydrocarbon-containing groups include a group of covalently bonded carbon atoms having the formula —$(CH_2)_m CH_3$, wherein m is 0 or an integer in the range of 1 to 5. Exemplary groups include methyl, ethyl, propyl, isopropyl, n-butyl, isobutyl, and t-butyl.

Additional chemistry can be present between the silyl ether group and the α(1→4)glucopyranose portion in the form of a linker group. The linker group can include hydrolyzable or non-hydrolyzable bonds.

The amount of silyl ether groups pendent from the glucopyranose polymer portion can be expressed, for example, by degree of substitution (i.e., number of hydroxyl groups per glucopyranose monomeric unit reacted with a compound that provides the silyl ether group) or by the weight to molar ratio between the poly-α(1→4)glucopyranose portion and the silyl ether groups, respectively. In some aspects, the silyl ether-modified hydrophobic polymer has a degree of substitution of pendent silyl ether groups in the range of about 0.04 to 1.2.

In some aspects, in the silyl ether-modified hydrophobic α(1→4)glucopyranose polymer, the poly-α(1→4)glucopyranose portion and the silyl ether group are present at a weight to molar ratio in the range of about 77 mgram:1 mmol to about 4053 mgram:1 mmol, respectively. In more specific aspects, the weight to molar ratio is in the range of about 150 mgram:1 mmol to about 2000 mgram:1 mmol, respectively.

The relationship between the hydrophobic portion and the silyl ether groups can also be determined and expressed, such as by the weight to molar ratio, respectively. In some aspects, in the silyl ether-modified hydrophobic α(1→4)glucopyranose polymer the hydrophobic portion and the silyl ether group are present at a weight to molar ratio in the range of about 50 mgram:1 mmol to about 4830 mgram:1 mmol, respectively. In more specific aspects, the weight to molar ratio is in the range of about 200 mgram:1 mmol to about 1250 mgram:1 mmol, respectively.

In exemplary modes of synthesis, the hydrophobic maltodextrin is derivatized with pendent silyl ether groups by first dissolving the hydrophobic maltodextrin in a halogenated organic solvent such as dichloromethane or chloroform at a concentration in the range of about 150 mg/mL to about 250 mg/mL. A nucleophilic catalyst such as 4-dimethylaminopyridine, is optionally added to the hydrophobic maltodextrin solution in an amount in the range of about 0.25 to about 0.6 mmol/gram. Next a hydroxyl-reactive silyl ether-containing compound, such as (3-isocyanatopropyl)triethoxysilane, is added to the hydrophobic maltodextrin, at a concentration in the range of about 0.1 mmol/gram to about 10 mmol/gram. The reaction takes place at room temperature in an inert atmosphere for a period of time. The reaction mixture is filtered and the solvent evaporated in vacuo.

In some aspects, the silyl ether-modified hydrophobic α(1→4)glucopyranose polymer can include monomeric units corresponding to one of the following polymer arrangements: (a) a silyl ether-modified hydrophobic α(1→4)glucopyranose polymer including formula II, (b) a silyl ether-modified hydrophobic α(1→4)glucopyranose polymer including formulas III and IV, (c) a silyl ether-modified hydrophobic α(1→4)glucopyranose polymer including formulas II and III, (d) a silyl ether-modified hydrophobic α(1→4)glucopyranose polymer including formulas II and IV, or (e) a silyl ether-modified hydrophobic α(1→4)glucopyranose polymer including formulas II, III, and IV, as shown below. For example, the silyl ether-modified hydrophobic α(1→4)glucopyranose polymer can include any one of arrangements (a)-(e) wherein the polymer includes modified glucopyranose units, as well as unmodified glucopyranose units.

Formula II is $[H^1]-[L^2]-[M^1]-[L^1]-[S^1]$, wherein $M^1$ is a monomeric unit of the poly-α(1→4)glucopyranose portion, $S^1$ is a silyl ether group, $H^1$ is a hydrocarbon segment, and $L^1$ and $L^2$ are linking groups.

Formula III is $[M^2]-[L^3]-[H^2]$ wherein $M^2$ is a monomeric unit of the poly-α(1→4)glucopyranose portion, $H_2$ is a hydrocarbon segment, and $L_3$ is a linking group.

Formula IV is [M³]-[L⁴]-[S²], wherein M³ is a monomeric unit of the poly-α(1→4)glucopyranose portion, S² is a silyl ether group, and L⁴ is a linking group.

For example, corresponding to one of arrangements (a), (c), (d), or (e), the silyl ether-modified hydrophobic α(1→4) glucopyranose polymer can have a monomeric unit of formula II: [H¹]-[L²]-[M¹]-[L¹]-[S₁], wherein M¹ is a monomeric unit of the poly-α(1→4)glucopyranose portion, S¹ is a silyl ether group, H¹ is a hydrocarbon segment, and L¹ and L² are linking groups.

For example, in some aspects, the silyl ether-modified hydrophobic α(1→4)glucopyranose polymer has a monomeric unit according to formula IIa:

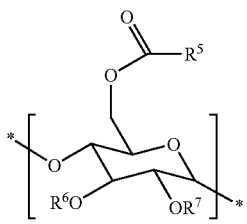

wherein $R^5$ is a $C_1$-$C_{18}$ hydrocarbon group, and more preferably —$(CH_2)_xCH_3$, wherein x is an integer in the range of 0-11; and
wherein $R^6$ and/or $R^7$ is:

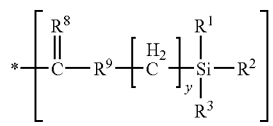

wherein $R^8$ is S or O, $R^9$ is C, O, N, or a covalent bond, y is an integer in the range of 2-8, $R^1$, $R^2$, and $R^3$ are independently selected from $R^4$ or $OR^4$, wherein $R^4$ includes a hydrocarbon group, such as a C1-C6-containing hydrocarbon group, or more specifically a linear or branched C1-C6 alkyl group, with the proviso that at least one of $R^1$, $R^2$, or $R^3$ is $OR^4$, and if one of $R^6$ or $R^7$ is not as defined above, then one of $R^6$ or $R^7$ is H.

In some aspects of formula IIa, $R^1$, $R^2$, and $R^3$, are all independently selected from $OR^4$, wherein $R^4$ is a C1-C6-containing hydrocarbon group, or more specifically, a linear or branched C1-C6 alkyl group.

In some aspects of formula IIa, one of $R^1$, $R^2$, or $R^3$ is $OR^4$, wherein $R^4$ is a C1-C6-containing hydrocarbon group, or more specifically a linear or branched C1-C6 alkyl group, and the other groups that are not $OR^4$ are independently selected from $R^4$.

Corresponding to one of arrangements (b), (c), or (e), the silyl ether-modified hydrophobic α(1→4)glucopyranose polymer can have a monomeric unit of formula III: [M²]-[L³]-[H²], wherein M² is a monomeric unit of the poly-α(1→4)glucopyranose portion, H² is a hydrocarbon segment, and L³ is a linking group.

For example, in some aspects, the silyl ether-modified hydrophobic α(1→4)glucopyranose polymer has a monomeric unit according to formula IIa:

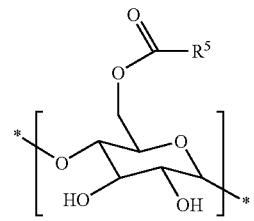

wherein $R^5$ is $C_1$-$C_{18}$ hydrocarbon group, and more preferably —$(CH_2)_xCH_3$, wherein x is an integer in the range of 0-11.

Corresponding to one of arrangements (b), (d), or (e), the silyl ether-modified hydrophobic α(1→4)glucopyranose polymer can have a monomeric unit of formula IV: [M³]-[L⁴]-[S²] wherein M³ is a monomeric unit of the poly-α (1→4)glucopyranose portion, S² is a silyl ether group, and L⁴ is a linking group.

For example, in some aspects, the silyl ether-modified hydrophobic α(1→4)glucopyranose polymer has a monomeric unit according to formula IVa:

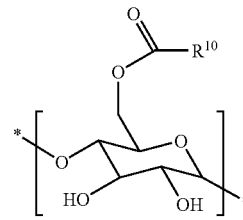

wherein $R^{10}$ is

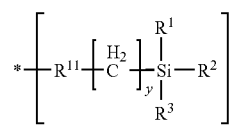

wherein $R^{11}$ is C, O, N, or a covalent bond, y is an integer in the range of 1-6, and $R^1$, $R^2$, and $R^3$ are independently selected $R^4$ and $OR^4$, wherein $R^4$ includes a hydrocarbon group, such as a C1-C6-containing hydrocarbon group, or more specifically a linear or branched C1-C6 alkyl group, with the proviso that at least one of $R^1$, $R^2$, or $R^3$ is $OR^4$.

In some aspects the silyl ether-containing hydrophobic α(1→4)glucopyranose polymer includes a derivatized monomeric unit of formula VII:

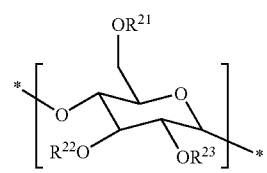

wherein one or more of $R^{21}$, $R^{22}$, and/or $R^{23}$ is according to formula VIII:

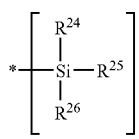

wherein one or more of $R^{24}$, $R^{25}$, and/or $R^{26}$ are independently selected from and include $C_1$-$C_{18}$ hydrocarbon groups, with the proviso that the total number of carbon atoms in $R^{24}$, $R^{25}$, and/or $R^{26}$ is at least three. Hydrophobic α(1→4)glucopyranose polymer containing these silyl ether linking groups are also described in commonly assigned and copending U.S. Application Ser. No. 61/247,402 (filed Sep. 30, 2009; Kurdyumov).

In some aspects of formula IVa, $R^1$, $R^2$, and $R^3$, are all independently selected from $OR^4$, wherein $R^4$ includes a hydrocarbon group, such as a C1-C6-containing hydrocarbon group, or more specifically a linear or branched C1-C6 alkyl group.

In some aspects of formula IVa, one of $R^1$, $R^2$, or $R^3$ is $OR^4$, wherein $R^4$ is includes a hydrocarbon group, such as a C1-C6-containing hydrocarbon group, or more specifically a linear or branched C1-C6 alkyl group, and the other groups that are not $OR^4$ are independently selected from $R^4$.

As shown, the derivatized monomers of formulas II-IV include linking groups $L^1$-$L^4$ that link either the hydrophobic group containing the hydrocarbon segment and/or the silyl ether group to the glycopyranose monomeric unit. In some cases, the linking group is hydrolyzable (e.g., non-enzymatically hydrolysable). For example, one or more of the linking groups (e.g., one or more of $L^1$-$L^4$) includes an ester, carbonate ester, or silyl ether group.

The silyl ether-modified hydrophobic α(1→4)glucopyranose polymer has the properties of being soluble in a variety of solvents that are commonly used for dissolving hydrophobic polymers. The solubility of the silyl ether-modified hydrophobic α(1→4)glucopyranose polymer in a solvent will depend on factors such as the level of derivation with the hydrophobic groups, the level of derivation with the silyl ether groups, as well as the particular solvent or combination of solvents used.

Exemplary solvents or dispersant include, but are not limited to, alcohols (e.g., methanol, ethanol and isopropanol), alkanes (e.g., halogenated or unhalogenated alkanes such as hexane, methylene chloride and chloroform), ethers (e.g., tetrahydrofuran (THF)), ketones (e.g., acetone, methyl ethyl ketone, methyl isobutyl ketone), aromatic compounds (e.g., toluene and xylene), nitriles (e.g., acetonitrile), and ester (e.g., ethyl acetate and butyl acetate).

Within a particular solvent, the silyl ether-modified hydrophobic α(1→4)glucopyranose polymer may be determined to be soluble (having a solubility of at least 1 part agent per from 10 to 30 parts solvent), freely soluble (having a solubility of at least 1 part agent per from 1 to 10 parts solvent), or very soluble (having a solubility of greater than 1 part agent per 1 part solvent). These descriptive terms for solubility are standard terms used in the art (see, for example, *Remington: The Science and Practice of Pharmacy*, 20th ed. (2000), Lippincott Williams & Wilkins, Baltimore Md.). The silyl ether-modified hydrophobic α(1→4)glucopyranose polymer has the properties of being insoluble in water. The term for insolubility is a standard term used in the art, and meaning 1 part solute per 10,000 parts or greater.

In some aspects, a silyl ether-modified hydrophobic α(1→4)glucopyranose polymer having a molecular weight within a predetermined size range is used. Unless otherwise noted, the molecular weight of silyl ether-modified hydrophobic α(1→4)glucopyranose polymer refers to the molecular weight of the fully derivatized polymer (i.e., including the pendent hydrophobic and silyl ether groups). The addition of hydrophobic groups and silyl ether groups to an α(1→4) glucopyranose polymer will generally cause a measurable increase in molecular weight of the polysaccharide from its underivatized, starting molecular weight. The amount increase in molecular weight can depend on one or more factors, such as the level of derivatization, and the chemical nature of the hydrophobic and silyl ether groups attached to the α(1→4)glucopyranose polymer.

In one aspect, the silyl ether-modified hydrophobic α(1→4)glucopyranose polymer has a molecular weight in the range of about 5 kDa to about 1000 kDa, and in more specific aspects a molecular weight in the range of about 25 kDa to about 500 kDa.

The silyl ether-modified hydrophobic α(1→4)glucopyranose polymer can be present in a liquid composition including a solvent suitable to dissolve the polymer ("a polymer solvent"), such as one or more described herein. Some preferred solvents include halogenated alkanes, such as methylene chloride and chloroform. Other solvents, including aromatic compounds such as toluene and xylene, ethers such as tetrahydrofuran, and amides such as dimethylformamide (DMF), can be used to dissolve the polymer. Combinations of one or more of these or other solvents can also be used.

Compositions including dissolved silyl ether-modified hydrophobic α(1→4)glucopyranose polymer in a solvent, or combination of solvents, can be used for the preparation of various articles, such as coatings, casting films, and implantable filaments.

It has also been found that the silyl ether-modified hydrophobic α(1→4)glucopyranose polymer can be provided in the form of an emulsion having good stability. A stable emulsion has been found particularly useful for the formation of polymeric matrices in various forms. The silyl ether-modified hydrophobic α(1→4)glucopyranose polymer can be present in either an oil-in-water-type of emulsion, or a water-in-oil-type of emulsion.

An oil-in-water-type of emulsion can include the silyl ether-modified hydrophobic α(1→4)glucopyranose polymer present in the dispersed phase. An oil-in-water-type of emulsion can be prepared by dissolving the polymer in a polymer solvent such as dichloromethane, chloroform, or another solvent that is immiscible with water. The solvated polymer can be added to an excess amount of continuous phase liquid, such as water or a water-based liquid. The continuous phase liquid can include one or more additional components that can stabilize the emulsion and promote the formation of discontinuous phase structures.

For example, the continuous phase liquid can include an emulsion stabilizer. An emulsion stabilizer can be present in the emulsion at a concentration of about 5 wt % or less, such as in the range of about 0.1 wt % to about 5 wt %.

It has also been discovered that halogenated arylboronic acids (described in commonly assigned and copending U.S. Application Ser. No. 61/247,408, entitled Emulsions Containing Arylborinic Acids, filed Sep. 30, 2009, to Slager), which include mono- and di-halogenated phenyl boronic acids, such as chlorophenylboronic acid and dichlorophenylboronic acid, provide remarkably stable emulsions including the silyl ether-modified hydrophobic α(1→4)glucopyranose polymers. The halogenated arylboronic acid is to the organic phase of the emulsion, either in the continuous phase in a oil-in-water-type of emulation, or the discontinuous phase of the water-in-oil-type of emulsion. In some aspects, the halogenated arylboronic acids emulsion stabilizer is added at a concentration in the range of about 0.005 wt % to about 5 wt %, and more specifically in the range of about 0.02 wt % to about 1 wt %.

With the addition of a halogenated arylboronic acid emulsion stabilizer, the silyl ether-modified hydrophobic α(1→4) glucopyranose polymer-containing emulsions have been found in stable form (i.e., the emulsion droplets do not coalesce to form two distinct continuous phases) for periods greater than about 24 hours, or greater than about 170 hours, such as up to about 670 hours.

To form a water-in-oil-type of emulsion, water or a water-based liquid can be dispersed in a continuous phase liquid, such as dichloromethane or chloroform, having the solubilized silyl ether-modified hydrophobic α(1→4)glucopyranose polymer.

After the discontinuous phase and continuous phase liquids are mixed, the composition can be agitated, such as in a homogenizer, to promote emulsion formation. After the emulsion has been formed, it can be used in the process for the formation of polymeric matrix in a certain form (herein referred to as an "article," that includes the polymeric matrix formed from the silyl ether-modified hydrophobic α(1→4) glucopyranose polymer).

The silyl ether-modified hydrophobic α(1→4)glucopyranose polymer can be used to form articles that are wholly or partially degradable. A partially degradable article can be an article that has a biostable portion, such as a biostable body member, and a biodegradable portion, such as a biodegradable coating.

The polymeric matrices formed from the silyl ether-modified hydrophobic α(1→4)glucopyranose polymers can be used in many medical applications. These include drug delivery medical applications, as well as applications where drug delivery is not required. The applications can involve short term or long-term treatment of various conditions.

In some aspects, the silyl ether-modified hydrophobic α(1→4)glucopyranose polymer is used to form a body member, or a portion of a body member, of an implantable medical article. In these aspects, a degradable body member, or portion thereof, can provide mechanical properties at the implantation site and can maintain these mechanical properties until they are no longer needed. After a period of time in the body, the body member is degraded to an extent that the mechanical properties are no longer provided, and the degraded components of the article are processed by the body.

In some embodiments, the body member of the medical article slowly degrades and transfers stress at the appropriate rate to surrounding tissues as these tissues heal and can accommodate the stress once borne by the body member of the medical article. The medical article can optionally include a coating or a bioactive agent to provide one or more additional functional features. However, a coating or bioactive agent may not required in order for the article to be of use at the treatment site. A biodegradable stent structure formed from the silyl ether-modified hydrophobic α(1→4)glucopyranose polymer is an example of a body member of an implantable device.

The article can also comprise filaments and fibers, such as microfibers and/or nanofibers that are formed from the silyl ether-modified hydrophobic α(1→4)glucopyranose polymer. The filaments or fibers can be included in, or associated with, various articles including implantable medical articles. The filaments or fibers may be prepared with a bioactive agent to provide one or more additional functional features.

In another aspect of the invention, the silyl ether-modified hydrophobic α(1→4)glucopyranose polymer is used to form a coated layer on a surface of a medical article. The hydrophobic α(1→4)glucopyranose polymer with reacted silyl ether groups can be present in one or more coated layers on all or a portion of the surface of the device. A "coating," as used herein, can include one or more "coated layers", each coated layer including one or more coating materials. In some cases, the coating can be formed of a single layer of material that includes the silyl ether-modified hydrophobic α(1→4)glucopyranose polymer. In other cases, the coating includes more than one coated layer, at least one of the coated layers including the silyl ether-modified hydrophobic α(1→4)glucopyranose polymer. If more than one layer is present in the coating, the layers can be composed of the same or different materials.

In some aspects, the silyl ether group is reacted with a material on the surface of article, such as a medical device, to form a coated layer. The hydrophobic α(1→4)glucopyranose polymer becomes bonded to the material surface via a siloxy group.

For the formation of a coating, a solution containing the silyl ether-modified hydrophobic α(1→4)glucopyranose polymer can be applied to the device surface and allowed to react.

In some aspects, a coating can be formed that includes formula V:

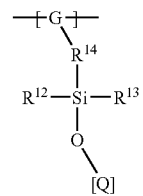

In formula V, G represents a monomeric unit of the hydrophobic α(1→4)glucopyranose polymer, Q represents an atom of the substrate material, or an atom of another polymer in the coating, $R^{12}$ and $R^{13}$ are independently selected from $R^4$ and $OR^4$, wherein $R^4$ includes a hydrocarbon group, such as a C1-C6-containing hydrocarbon group, or more specifically a linear or branched C1-C6 alkyl group, and $R^{14}$ is a group linking the silane atom to the monomeric unit. In some aspects $R^{14}$ is:

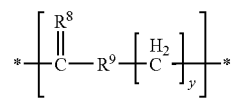

wherein $R^8$, $R^9$, and y are defined as in formula II herein; or

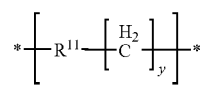

wherein $R^{11}$ and y are defined as in formula IV herein.

Optionally, in addition to the pendent silane-containing group bonding the polymer to the substrate material, the coating can also include polymer-polymer crosslinking. Optional polymer-polymer crosslinking can be established by condensation reaction between the silyl ether groups, resulting in covalent bonding via pendent silane-containing groups.

Bioactive agents can also be associated with the coating. The coating can include a coated layer formed using the silyl ether-modified hydrophobic α(1→4)glucopyranose polymer.

In a preferred arrangement, a bioactive agent is present in a second coated layer. The second coated layer does not necessarily include the silyl ether-modified hydrophobic α(1→4)glucopyranose polymer. However, the second coated layer can be associated with a first coated layer formed using the silyl ether-modified hydrophobic α(1→4)glucopyranose polymer. For example, in one aspect, the first coated layer formed using the silyl ether-modified hydrophobic α(1→4) glucopyranose polymer is a tie layer on the surface of a device, and the second coated layer includes a matrix-forming polymer and bioactive agent.

A device having a bioactive-agent releasing coating, wherein the silyl ether-modified hydrophobic α(1→4)glucopyranose polymer is a tie layer can be formed using the following exemplary process. First a device having surface that is reactive with hydrolyzed silyl ether groups is obtained. The device material may inherently have groups that are able to bond with the hydrolyzed silyl ether groups; examples of these types of device materials include stainless steel, nitinol, cobalt chrome, and other metals with an inherent oxide layer. The device can also include hydroxyl functionalities at the surface. The hydroxyl functionalities can be provided by the device material, or by a base layer of polymeric material.

In some cases, the device surface is pretreated to introduce groups that are reactive with silyl ether groups. For example, some untreated metal surfaces will not be reactive with silyl ethers or silanols. The surface of a device made from such metals can be functionalized to provide groups that are able to react. For example, the metal surface can be treated with a gas or a solution containing a base such as NaOH to create oxygen-containing groups on the device surface. Oxygen-containing functional groups such as —OH, —OOH, —CO, and —O can react with the silyl ether groups to provide a covalently bonded linkage between the device material and the hydrophobic α(1→4)glucopyranose polymer.

The bonding reaction using the silyl ether-modified hydrophobic α(1→4)glucopyranose polymer can be carried out in aqueous conditions (for example, with the formation and hydrolysis of silanol groups), or in non-aqueous conditions. Bonding can proceed via a condensation reaction. For example, a composition (such as a solution) including the silyl ether-modified hydrophobic α(1→4)glucopyranose polymer is disposed on the surface, and the silyl ether groups hydrolyze and react with the oxygen-containing groups to form covalent siloxy bonds between the device surface and the hydrophobic α(1→4)glucopyranose polymer, thereby forming a polymeric tie layer. Polymer-polymer crosslinking through reacted silyl ether groups may also occur. Therefore, the polymeric matrix can include α(1→4)glucopyranose polymer covalently bonded to the device surface via silane-containing groups, as well as crosslinked α(1→4)glucopyranose polymer bonded via silane-containing groups.

After the tie layer is formed, a composition including a matrix forming polymer and a bioactive agent is disposed on the polymeric tie layer, and a polymeric bioactive agent-releasing layer is formed. The matrix-forming polymer of the bioactive agent-releasing layer can also be a hydrophobic polymer, a degradable polymer, or both hydrophobic and degradable. In some instances the hydrophobic polymer is a hydrophobic α(1→4)glucopyranose polymer without pendent silane ether groups. A hydrophobic matrix-forming polymer may be able to blend into the tie layer to a certain extent, thereby providing a more durable coating where the materials of the bioactive agent-releasing layer become partially mixed with the tie layer.

Optionally, a coating can be formed wherein the bioactive agent is present in a polymeric matrix formed using the silyl ether-modified hydrophobic α(1→4)gluco-pyranose polymer. The coating can be prepared, or the bioactive chosen, in such a way to minimize or prevent reaction of the hydrolyzed silyl ether groups with the bioactive agent. For example, one may use a bioactive agent that does not present groups that are reactive with the silyl ether groups or hydrolyzed silyl ether groups.

A coating composition, with or without bioactive agent, can be applied to a medical device using standard techniques to cover the entire surface of the device, or a portion of the device surface. If more than one coated layer is applied to a surface, it is typically applied successively. For example, a coated layer can be formed by, for example, dipping, spraying, bushing, or swabbing a coating composition including the silyl ether-modified hydrophobic α(1→4)glucopyranose polymer on the article to form a layer, and then activating the polymer with water to cause hydrolysis and reaction of the silyl ether groups. The process can be repeated to provide a coating having multiple coated layers, wherein at least one layer includes the reacted silyl ether-modified hydrophobic α(1→4)glucopyranose polymer. The compositions of the present invention are suitable for use in a spray coating processes.

An exemplary spray coating process and apparatus that can be used for coating implantable medical articles using the compositions of the present invention is described in U.S. Pat. No. 7,192,484 (Chappa et al.)

A composition that includes the silyl ether-modified hydrophobic α(1→4)glucopyranose polymer can be spray coated directly onto the surface of a body member of a medical article, or can be spray coated onto a surface that includes one or more coated layers of material previously formed on the body member.

The following list of medical articles is provided to illustrate various medical articles that can that can be associated with a polymeric matrix made using the silyl ether-modified hydrophobic α(1→4)glucopyranose polymer. These types of articles are typically introduced temporarily or permanently into a mammal for the prophylaxis or treatment of a medical condition. For example, these articles can be introduced subcutaneously, percutaneously or surgically to rest within an organ, tissue, or lumen of an organ, such as arteries, veins, ventricles, or atria of the heart.

Exemplary medical articles include vascular implants and grafts, grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septic defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and stent graft catheters; anastomosis devices and anastomotic closures; aneurysm exclusion devices; biosensors; cardiac sensors; birth control devices; breast implants; infection control devices; membranes; tissue scaffolds; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff, sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; and biliary drainage products.

In some aspects the polymeric matrix made using the silyl ether-modified hydrophobic α(1→4)glucopyranose polymer is associated with an ophthalmic article. For example, the matrix can be used as a coating on the surface of an ophthalmic article, or as a filament or drug delivery depot configured for placement at an external or internal site of the eye. In some aspects, the articles can be utilized to deliver a bioactive agent to an anterior segment of the eye (in front of the lens), and/or a posterior segment of the eye (behind the lens). Illustrative intraocular devices include, but are not limited to, those described in U.S. Pat. Nos. 6,719,750 B2 (Varner et al.) and 5,466,233 ("Tack for Intraocular Drug Delivery and Method for Inserting and Removing Same," Weiner et al.) Illustrative ophthalmic devices for subretinal application include, but are not limited to, those described in U.S. Patent Publication No. 2005/0143363 (de Juan et al.).

A polymeric matrix made using the shy' ether-modified hydrophobic α(1→4)glucopyranose polymer can be associated with a device formed of a non-biodegradable material. For example, a coating can be formed on a body member of a medical article that is partially or entirely fabricated from a plastic polymer. Plastic polymers include those formed of synthetic polymers, including oligomers, homopolymers, and copolymers resulting from either addition or condensation polymerizations. Examples of suitable addition polymers include, but are not limited to, acrylics (e.g., methyl acrylate) and vinyls (e.g., ethylene). Examples of condensation polymers include, but are not limited to, nylons (e.g., polycaprolactam) and also polyurethanes, polycarbonates, polyamides, polysulfones, poly(ethylene terephthalate), polydimethylsiloxanes, and polyetherketones.

The polymeric matrix can also be associated with an implantable medical article partially or entirely fabricated from a degradable polymer. The article can degrade in an aqueous environment, such as by simple hydrolysis, or can be enzymatically degraded. Examples of classes of synthetic polymers that can be used to form the structure of a degradable article include polyesters, polyamides, polyurethanes, polyorthoesters, polycaprolactone (PCL), polyiminocarbonates, aliphatic carbonates, polyphosphazenes, polyanhydrides, and copolymers thereof. As an example, the hydrophobic polysaccharide can provide a barrier coating to articles fabricated from polylactide or copolymers thereof. The coating can shield the article during a portion or all of a desired period of treatment. The coated article can still be fully degradable.

The polymeric matrix can also be associated with an implantable medical article that is partially or entirely fabricated from a metal. Although many devices or articles are constructed from substantially all metal materials, such as alloys, some may be constructed from both non-metal and metal materials, where at least a portion of the surface of the device is metal.

Commonly used metals include platinum, gold, or tungsten, as well as other metals such as rhenium, palladium, rhodium, ruthenium, titanium, nickel, and alloys of these metals, such as stainless steel, titanium/nickel, nitinol alloys, cobalt chrome alloys, non-ferrous alloys, and platinum/iridium alloys. One exemplary alloy is MP35. The metal surface can be pretreated to introduce groups that are reactive the hydrolyzed silyl ether groups. For example, the metal surface can be treated with a gas or a basic solution (containing a base like NaOH) to create oxygen-containing groups on the device surface. Oxygen-containing functional groups such as —OH, —OOH, —CO, and —O can react with the hydrolyzed silyl ether groups to provide a covalently bonded linkage between the metal device and the hydrophobic α(1→4)glucopyranose polymer.

In some aspects a biodegradable coating is formed on the surface of an erodible implantable medical device formed from of a metal. For example, the biodegradable coating can be formed on a magnesium alloy stent that can be corroded following placement in a subject (see, for example, De Mario, C. et al. (2004) *J. Interv. Cardiol.*, 17(6):391-395, and Heublein, B., et al. (2003) *Heart;* 89:651-656). The erodible implantable medical device can be associated with a bioactive agent, if desired.

In aspects where the structure of the implantable medical article is fabricated from a material that is erodible or degradable, an in vivo lifetime of the article can be determined. Using the silyl ether-modified hydrophobic α(1→4)glucopyranose polymer, a biodegradable coating can be formed the surface of these erodible or degradable articles to prolong their in vivo lifetime. For example, a coating formed from the silyl ether-modified hydrophobic α(1→4)glucopyranose polymer can provide a hydrophobic biodegradable barrier which protects a degradable body member from degradation for a period of time. Upon degradation of the barrier, the body member can quickly degrade. The in vivo lifetime is a period of time starting upon placement of the coated article at a target location, and ending when the coated article is completely degraded at the target location.

Other contemplated biomaterials include ceramics including, but not limited to, silicon nitride, silicon carbide, zirconia, and alumina, as well as glass, silica, and sapphire. Combinations of ceramics and metals can also be coated.

The biodegradable matrix can also be associated with an article having a porous structure, such as one formed of a fabric or that has fabric-like qualities. The porous structure can be formed from textiles, which include woven materials, knitted materials, and braided materials. Particularly useful textile materials are woven materials which can be formed using any suitable weave pattern known in the art.

The porous structure can be that of a graft, sheath, cover, patch, sleeve, wrap, casing, and the like, including many of the medical articles described herein. These types of articles can function as the medical article itself or be used in conjunction with another part of a medical article.

Other particular contemplated porous structures include grafts, particularly grafts having textured exterior portions. Examples of textured grafts include those that have velour-textured exteriors, with textured or smooth interiors. Grafts constructed from woven textile products are well known in the art and have been described in numerous documents, for example, U.S. Pat. Nos. 4,047,252; 5,178,630; 5,282,848; and 5,800,514.

The term "bioactive agent," refers to an inorganic or organic molecule, which can be synthetic or natural, that causes a biological effect when administered in vivo to an animal, including but not limited to birds and mammals, including humans.

A partial list of bioactive agents is provided below. According to embodiments of the present invention, one may choose one or more of the bioactive agents to be included in an article or coating is associated with a matrix formed from the silyl ether-modified hydrophobic α(1→4)glucopyranose polymer. A comprehensive listing of bioactive agents, in addition to information of the water solubility of the bioactive agents, can be found in *The Merck Index*, Thirteenth Edition, Merck & Co. (2001).

Articles and coatings prepared according to the invention can be used to release bioactive agents falling within one or more of the following bioactive agent classes. These classes include, but are not limited to: ACE inhibitors, actin inhibitors, analgesics, anesthetics, anti-hypertensives, anti polymerases, antisecretory agents, anti-AIDS substances, antibiotics, anti-cancer substances, anti-cholinergics, anti-coagulants, anti-convulsants, anti-depressants, anti-emetics, antifungals, anti-glaucoma solutes, antihistamines, antihypertensive agents, anti-inflammatory agents (such as NSAIDs), anti metabolites, antimitotics, antioxidizing agents, anti-parasite and/or anti-Parkinson substances, anti-proliferatives (including antiangiogenesis agents), anti-protozoal solutes, anti-psychotic substances, anti-pyretics, antiseptics, anti-spasmodics, antiviral agents, calcium channel blockers, cell response modifiers, chelators, chemotherapeutic agents, dopamine agonists, extracellular matrix components, fibrinolytic agents, free radical scavengers, growth hormone antagonists, hypnotics, immunosuppressive agents, immunotoxins, inhibitors of surface glycoprotein receptors, microtubule inhibitors, miotics, muscle contractants, muscle relaxants, neurotoxins, neurotransmitters, polynucleotides and derivatives thereof, opioids, photodynamic therapy agents, prostaglandins, remodeling inhibitors, statins, steroids, thrombolytic agents, tranquilizers, vasodilators, and vasospasm inhibitors.

In some cases, the hydrophobic groups pendent from the α(1→4)glucopyranose backbone have properties of a bioactive agent. In these aspects, the hydrophobic group/bioactive agent can be hydrolyzed from the α(1→4)glucopyranose backbone and released from the matrix to provide a therapeutic effect in a subject. An example of a therapeutically useful compound having a hydrocarbon segments is butyric acid, which has been shown to elicit tumor cell differentiation and apoptosis, and is thought to be useful for the treatment of cancer and other blood diseases. Other illustrative compounds comprising hydrocarbon segments include valproic acid and retinoic acid. Retinoic acid is known to possess antiproliferative effects and is thought to be useful for treatment of proliferative vitreoretinopathy (PVR). Another illustrative compound that can be coupled to the polysaccharide backbone is a corticosteroid. An exemplary corticosteroid is triamcinolone. One method of coupling triamcinolone to a natural biodegradable polymer is by employing a modification of the method described in Cayanis, E. et al., *Generation of an Auto-anti-idiotypic Antibody that Binds to Glucocorticoid Receptor*, The Journal of Biol. Chem., 261(11): 5094-5103 (1986). Triamcinolone hexanoic acid is prepared by reaction of triamcinolone with ketohexanoic acid; an acid chloride of the resulting triamcinolone hexanoic acid can be formed and then reacted with the polysaccharide, such as maltodextrin or polyalditol, resulting in pendent triamcinolone groups coupled via ester bonds to the polysaccharide.

Thin polymer free standing films can be prepared from a composition including the silyl ether-modified hydrophobic α(1→4)glucopyranose polymer. In some modes of practice, free standing films are prepared by spin casting the polymer on a glass substrate. The formed films can be floated on a water surface, and subsequently handled. The free standing films can be shaped (such as by cutting) to provide a desired configuration.

In other aspects, the silyl ether-modified hydrophobic α(1→4)glucopyranose polymer is used to form an implantable or injectable medical article which also includes a bioactive agent. The implant may not have any distinct mechanical properties, such as would be apparent with an intravascular prosthesis, but rather provides a mechanism to deliver the bioactive agent to a particular portion of the body. The implant can have a defined structure and size that is appropriate for its use at a desired location in the body.

In some aspects the an implantable or injectable medical article includes a matrix formed of the silyl ether-modified hydrophobic α(1→4)glucopyranose polymer which modulates the release of the bioactive agent from the article. In some cases, the matrix is in the form of a barrier layer that the bioactive agent passes through before becoming available to the subject. Such a barrier layer can be in the form of a shell of polymeric material encapsulating a core comprising bioactive agent.

A medical implant having a defined structure can be formed by any suitable process, including molding, extruding, shaping, cutting, casting, and the like. In some aspects, silyl ether groups of the modified hydrophobic α(1→4)glucopyranose polymer are reacted to crosslink the hydrophobic α(1→4)glucopyranose polymers via a siloxane linkage. Polymer-polymer crosslinking via siloxane linkages can be useful for formation of various implants, and silane bonding to a different substrate material is not required.

Crosslinking can occur by hydrolysis of a silyl ether group, and subsequent reaction with a silane group through a condensation reaction. Silane-containing groups associate by hydrogen bonding, and then an increase in temperature can promote the condensation reaction. Crosslinking can also occur through formation of a silanol group following loss of the alkyl radical, and subsequent reaction with a silane group accompanies loss of a water molecule. The extent of crosslinking can be modulated by the reaction conditions including time, heat, etc.

In some aspects, a polymeric matrix can be formed that includes the following formula VI:

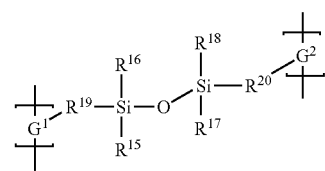

In formula VI, $G^1$ and $G^2$ represent monomeric units of different hydrophobic α(1→4)glucopyranose polymers, $R^{15}$, $R^{16}$, $R^{17}$, and $R^{18}$ are independently selected from $R^4$ and $OR^4$, wherein $R^4$ includes a hydrocarbon group, such as a C1-C6-containing hydrocarbon group, or more specifically a linear or branched C1-C6 alkyl group, and $R^{19}$ and $R^{20}$ are groups linking the silane atoms to the monomeric units. In some aspects $R^{19}$ and $R^{20}$ are independently selected from:

$$*+\left[\begin{array}{c}R^8\\\|\\C-R^9\end{array}\left[\begin{array}{c}H_2\\C\end{array}\right]_y\right]*$$

wherein $R^8$, $R^9$, and y are defined as in formula II herein; or $$*+\left[R^{11}+\left[\begin{array}{c}H_2\\C\end{array}\right]_y\right]*$$

wherein $R^{11}$ and y are defined as in formula IV herein.

Formula VI shows the crosslinking of two hydrophobic α(1→4)glucopyranose polymers through their respective monomeric unit via a crosslinking chemistry that has silane groups. However, crosslinking of more than two hydrophobic α(1→4)glucopyranose polymers can occur if the polymer includes pendent groups having two or more silyl ether groups.

In other aspects, the silyl ether-modified hydrophobic α(1→4)glucopyranose polymer is used to form a microparticle.

Microparticles including a reacted silyl ether-modified hydrophobic α(1→4)glucopyranose polymer can be formed using the oil-in-water-type of emulsion, or the water-in-oil-type of emulsion described herein.

In some modes of practice, microparticles are formed starting with the silyl ether-modified hydrophobic α(1→4)glucopyranose dissolved in a suitable solvent, such as dichloromethane or chloroform, optionally mixed with a secondary solvent, such as an alcohol like methanol. Optionally, and preferably, an emulsion stabilized can be added to the polymer solution, such as a halogenated arylboronic acid, like dichlorophenylboronic acid (DPBA) as described herein. Next, the polymer solution can be combined with water. For water-in-oil-types of emulsions an amount of water can be added that is a fraction of the overall amount of polymer solution (such as in the range of about 1:500 to about 1:10 v/v water:polymer solution). The mixture is then emulsified using a high-speed blender. The addition of water and emulsion blending promotes the formation of microdroplets of water, which are surrounded by the silyl ether-modified hydrophobic α(1→4)glucopyranose which crosslinks and begins the formation of a crosslinked polymer shell around the microdroplets. A portion of this emulsion is then taken and dispersed in an aqueous solution to isolate the shelled microdroplets and promote further crosslinking of the silyl ether-modified hydrophobic α(1→4)glucopyranose shell.

In another mode of forming microparticles, the polymer solution containing the silyl ether-modified hydrophobic α(1→4)glucopyranose dissolved in a suitable solvent is added to an excess volume of an aqueous solution. A suitable excess volume can be about 10 times the volume of the polymer solution or greater. The aqueous solution can include a agent that promotes formation of the microparticles, such as poly(vinyl alcohol). The mixture is then emulsified using a high-speed blender. Solid particles of reacted silyl ether-modified hydrophobic α(1→4)glucopyranose polymer are formed.

In some aspects, the microparticle also includes a bioactive agent, and the microparticle can be used to deliver this bioactive agent following implantation or injection. Generally, microparticles have a size in the range of 5 nm to 100 μm in diameter, and are spherical or somewhat spherical in shape.

Microparticles with a bioactive agent containing a core and a polymeric shell can also be formed. In yet another mode of practice, the polymer solution containing the silyl ether-modified hydrophobic α(1→4)glucopyranose dissolved in a suitable solvent also includes microparticles that are formed including a bioactive agent. Generally, the bioactive agent-containing microparticles are not dissolvable in the solvent that is used to solubilize the hydrophobic glucopyranose polymer. The polymer/microparticle mixture is then added to an excess volume of an aqueous solution. The mixture is then emulsified using a high-speed blender. Microparticles having a bioactive agent-containing core and a reacted silyl ether-modified hydrophobic α(1→4)glucopyranose polymeric shell are formed.

Bioactive agents incorporated into the microparticles formed using these techniques can release a desired amount of the agent over a predetermined period of time. The bioactive agent can be released from the biodegradable microparticle upon degradation of the biodegradable microparticle in vivo.

Microparticles that are formed from the silyl ether-modified hydrophobic α(1→4)glucopyranose polymer can also be processed into other forms to provide an implantable or injectable article is a desired configuration or shape. Given this, the current invention also contemplates microparticles formation as a general way to react and crosslink the silyl ether-modified hydrophobic α(1→4)glucopyranose polymer to form a desired hydrophobic degradable polymeric article. For example, the various oil-in-water-types of emulsions, or the water-in-oil-types of emulsions described herein can be used to form microparticles having crosslinked polymers, which are subsequently processed to a second desired form. The method can involve a step of removing all or a portion of water from the polymer-containing compositions (e.g., a drying step) that promotes formation of siloxane bonds.

Medical articles associated with a matrix formed from the silyl ether-modified hydrophobic α(1→4)glucopyranose polymer can be treated to sterilize one or more parts of the article, or the entire medical article. Sterilization can take place prior to using the medical article and/or, in some cases, during implantation of the medical article.

In some aspects, the invention provides a method for delivering a bioactive agent from coating or article associated with a matrix formed from the silyl ether-modified hydrophobic α(1→4)glucopyranose polymer. The bioactive agent can be present in a matrix formed from the silyl ether-modified hydrophobic α(1→4)glucopyranose polymer, or associated with a different portion of the article. For example, the matrix formed from the silyl ether-modified hydrophobic α(1→4) glucopyranose polymer may provide a barrier that the bioactive agent passes through, or the bioactive agent is releasable from a different polymeric layer that is also associated with the article.

In performing the method, the article is placed in a subject. Upon exposure to body fluid the bioactive agent is released from a portion of the article. In some cases, depending on the arrangement of the matrix formed from the silyl ether-modified hydrophobic α(1→4)glucopyranose polymer, the article is subjected to degradation by non-enzymatic hydrolysis, enzymatic amylase activity, or both. A carbohydrase can promote the degradation of the polymeric matrix. Degradation may occur before, during, or after the release of the bioactive agent. Examples of carbohydrases that can specifically degrade natural biodegradable polysaccharide coatings include α-amylases, such as salivary and pancreatic α-amylases; disaccharidases, such as maltase, lactase and sucrase; trisaccharidases; and glucoamylase (amyloglucosidase).

Serum concentrations for amylase are estimated to be in the range of about 50-100 U per liter, and vitreal concentrations also fall within this range (Varela, R. A., and Bossart, G. D. (2005) *J Arm Vet Med Assoc* 226:88-92).

In some aspects, the carbohydrase can be administered to a subject to increase the local concentration, for example in the serum or the tissue surrounding the implanted or injected device or article, so that the carbohydrase may promote the degradation of the matrix. Exemplary routes for introducing a carbohydrase include local injection, intravenous (IV) routes, and the like. Alternatively, degradation can be promoted by indirectly increasing the concentration of a carbohydrase in the vicinity of the matrix, for example, by a dietary process, or by ingesting or administering a compound that increases the systemic levels of a carbohydrase.

In other cases, the carbohydrase can be provided on a portion of the article. For example the carbohydrase may be eluted from a portion of the article that does not include the matrix. In this aspect, as the carbohydrase is released it locally acts upon the coating to cause its degradation and promote the release of the bioactive agent.

The invention will be further described with reference to the following non-limiting Examples.

EXAMPLE 1

Fractionated Maltodextrin

Maltodextrin was purchased from Roquette, France (Glucidex™ 2, $MW_{ave}$ 320 kDa) or Grain Processing Corporation, Muscatine, Iowa (M040 $MW_{ave}$ 55 kDa). The 55 kDa maltodextrin was used as received. Glucidex™ 2 was further fractionated to a narrower polydispersity.

Glucidex™ 2 maltodextrin (MD; 500 g; DE=3 max) was dissolved in deionized water to a total volume of 5 L with stirring, and diafiltered using a 500 kDa molecular weight cut-off cassette, and the permeate (flow through) was kept. The permeate was then diafiltered using a 100 kDa weight cut-off cassette and the retentate was kept. The solution was concentrated down to 3 L and then lyophilized. 310 g of maltodextrin (100-500 kDa) was isolated (62% yield).

EXAMPLE 2

Hydrophobic Maltodextrin MD-Hex

Reagents were purchased from Aldrich and were used as received unless noted. Solvents were not pre-dried prior to reaction unless noted. Maltodextrin (20 g) from either the 55 kDa preparation or the 100-500 kDa preparation as described in Example 1 was taken up in anhydrous DMSO (200 mL). 1-methylimidazole (21 mL, 0.263 mol), was added to the maltodextrin solution, and stirred for 5 min. Hexanoic anhydride (50 mL, 0.217 mol) was then added to the reaction mixture, and stirring was continued for an additional 2 hr at room temperature. The reaction was quenched by pouring the reaction mixture into water (500 mL) at room temperature. The mixture was then blended in Waring blender for less then one minute. The product (maltodextrin-hex) formed a white solid which was collected by vacuum filtration and washed with water (10×100 mL). 21.7 g of product was obtained. To further purify maltodextrin-hex, it was dissolved in acetone and placed into 1,000 MWCO dialysis tubing and dialyzed against acetone (3×1 L) for 3 days at room temperature. Solution from dialysis tube was collected and solvent was removed in vacuo. The resulting white solid was dried in vacuo. The maltodextrin-hex products had a degree of substitution with hexanoate groups (DS-hex) of 1.5, and molecular weights (ave) of starting maltodextrin 55 kDa and 320 kDa.

Similar procedures were performed, with variation in the amount of hexanoic anhydride used. These procedures provided maltodextrin-hex products with degrees of substitution of hexanoate groups (DS-hex) of 0.9 and 2.1, and molecular weights (ave) of starting maltodextrin 120 kDa and 320 kDa, respectively.

EXAMPLE 3

Siloxy Ether Derivatized Hydrophobic Maltodextrin MD-Hex Silane

MD-Hex (DS-hex=0.9, 2.0 g), as described in Example 2, was placed into 50 mL oven-dried flask under inert atmosphere and dissolved in anhydrous $CH_2Cl_2$ (20 mL) at room temperature. DMAP (0.1 g, 0.819 mmol; 4-dimethylaminopyridine) was added to the MD-Hex solution and reaction mixture was allowed to stir for an additional 5 min. After this, 3-isocyanatopropyltriethoxysilane (4.0 mL, 16.2 mmol) was added via syringe over 30 sec. The mixture was allowed to stir for an additional 70 hr at room temperature under inert atmosphere. Reaction mixture was then filtered and the solvent evaporated in vacuo. The crude product, including the silylether modified MD-hex (MD-Hex-silane), was dissolved in acetone and placed into 12,000-14,000 MWCO dialysis tubing and dialyzed against acetone (3×1 L) for 3 days. Solution from dialysis tube was collected and the solvent was removed in vacuo. The resulting white solid was dried in vacuo, with the process providing 1.5 g of solid.

The levels of derivations of the MD-hex silane products are listed in Table 1.

EXAMPLE 4

Siloxy Ether Derivatized Hydrophobic Maltodextrin MD-Hex Silane

MD-Hex (DS=2.1, 3.0 g), as described in Example 2, was placed into a 50 mL oven-dried flask under inert atmosphere and dissolved in anhydrous $CHCl_3$ (25 mL) at room temperature. Next, 3-isocyanatopropyltriethoxysilane (0.1 mL, 0.404 mmol) was added via syringe to the MD-Hex solution and the reaction mixture was allowed to stir for additional 16 hr at room temperature under an inert atmosphere. The reaction mixture was then filtered, diluted with $CHCl_3$ to 150 mL and kept at 4° C. for further use.

The levels of derivations of the MD-hex silane products are listed in Table 1.

TABLE 1

| Polymer | MW maltodextrin | DS Hex | Theor DS Silane |
|---------|-----------------|--------|-----------------|
| A | 320 kDa | 1.5 | 1.2 |
| B | 55 kDa | 1.5 | 0.6 |
| C | 120 kDa | 0.9 | 2.1 |
| D | 320 kDa | 2.1 | 0.05 |
| E | 55 kDa | 1.5 | 0.04 |

EXAMPLE 5

MD-Hex Silane Device Coatings

Bare metal stents were rinsed with chloroform, dried, cleaned with a solution of NaOH in IPA (Enprep™), rinsed with water, dried, and then weighed.

A tie layer coating composition was prepared by dissolving MD-Hex-silane (MW$_{ave}$=320 kDa; DS-hex 2.1, DS-silane 0.05 from Example 4) in chloroform at a concentration of approximately 20 mg/mL. A drug-containing polymeric coating composition was prepared by mixing MD-Hex DS 2.5 (MW$_{ave}$=320 kDa) or MD-Hex DS 2.5 (or MW$_{ave}$=120 kDa) with sirolimus (67 wt % polymer, 33 wt % sirolimus), and then dissolving the mixture in acetone. The final concentration of the solution was 40 mg/mL total solids. All solutions were filtered (10 μm) before use.

Stents were coated using an ultrasonic spray coating process and apparatus as described in U.S. Pat. No. 7,192,484 (Chappa et al.). One group of stents was first coated with a solution of MD-Hex-silane to yield approximately 40 μg of coated MD-Hex-silane on each stent. The coating was dried under nitrogen to remove residual solvent. The samples were then briefly dipped in water and placed in an oven at 110° C. and allowed to cure for 60 min. Samples were then weighed to determine the mass of coating applied. Variations of this approach (with and without water dipping, curing for 10 vs. 60 min.) were also performed. A second group of stents were not provided with a MD-Hex-silane base coat (tie layer) and were left as bare metal.

Bare metal and MD-Hex-silane base coated stents were subsequently coated with a mixture of MD-Hex DS 2.5 (or MW$_{ave}$=320 kDa or 120 kDa) and sirolimus (67/33 wt/wt). Approximately 800 μg of coating material was applied by the spray coating process. Stents were dried under nitrogen to remove residual solvent and weighed.

Coated stents were crimped with a pneumatic crimp head onto 3.0/3.5 mm balloon catheters. The crimped stent/balloon assemblies were then immersed in 10 mM PBS, pH 7.4, 37° C. for 5 min after which a pressure of 10 atm was applied to the balloon in order to expand the stent. The catheter was removed and the stent was rinsed with water to remove salts, dried, and examined with SEM to evaluate coating integrity.

Figure 1B:
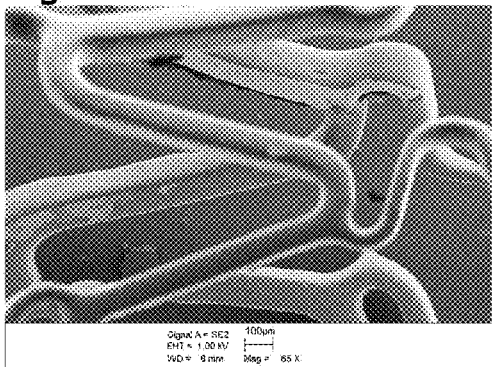
Figure 1C:
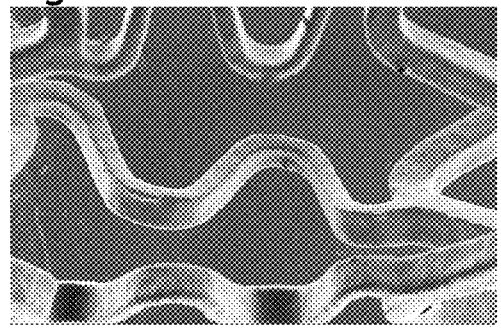
FIGS. 1C and 1D are micrographs of stents having a hydrophobic polymeric coating with a silyl ether-modified hydrophobic α(1→4)glucopyranose polymer tie layer, the micrographs taken after balloon expansion of the stents.

Without the MD-Hex-silane base coat, the MD-Hex DS 2.5/sirolimus coating showed significant delamination stent surface after mechanical expansion (FIG. 1A-1C). The majority of the delamination occurred on the lumen of the stent, where the coating was in contact with the balloon during expansion.

Figure 1D:
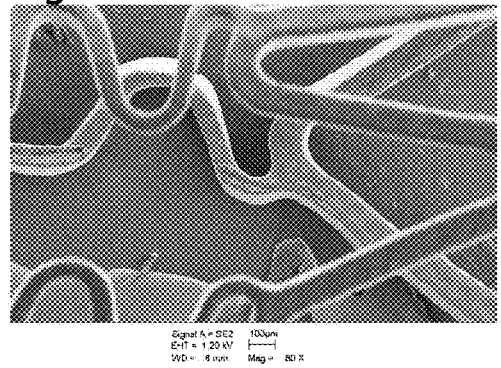

The MD-Hex-silane base coat (tie layer) improved the durability and physical appearance of the MD-Hex DS 2.5/sirolimus coating. Stents having the MD-Hex-silane base coat (tie layer) showed very little delamination on the lumen of the stent following balloon expansion (FIG. 1D-1F).

EXAMPLE 6

MD-Hex Silane Microparticles

MD-Hex-silane (polymer D in Table 1: 320 kDa, DS hex 2.1, DS silane 0.05 (theor.) was dissolved in chloroform at 20 mg/mL. The MD-Hex-silane solution in an amount of 500 μL was dispersed into 50 mL of 2% polyvinyl alcohol (PVA) in double distilled water (DDW) at 8000 rpm for 2 min using a high shear mixer (Silverson Machines Ltd., Chesham, UK). The dispersion was stirred for 2 hours to evaporate chloroform at room temperature with no vacuum. Particles were isolated by centrifugation in 15 mL conical tubes (3000 rpm for 15 mins). The water phase was decanted. Samples of the particles were put on a glass plate and dried under vacuum for several hours.

Microscope scans were made after vacuum drying. FIG. 2A shows MD-Hex-silane microparticles (untreated), and FIG. 2B shows MD-Hex-silane microparticles after a drop of dichloromethane was applied to the sample.

EXAMPLE 7

MD-Hex Silane Emulsions

Emulsion formulations were attempted for mixtures of MD-Hex silane solutions with aqueous solutions having various additives.

A MD-Hex-silane solution was prepared by dissolving MD-Hex-silane (polymer D in Table 1: 56 kDa, DS hex 1.5, DS silane 0.04 (theor.)) in dichloromethane at 10 mg/mL. The following aqueous solutions or suspensions were made using DDW as shown in Table 2.

TABLE 2

| Solution | Component | Amount | Notes |
|---|---|---|---|
| A | (water only) | | |
| B | Sodium borate (borax) | 10 mg/mL | |
| C | Boric acid | 10 mg/mL | |
| D | Phenylboronic acid | 10 mg/mL | Dissolved using sonic bath |
| E | 3,5-dichlorophenylboronic acid | 10 mg/mL | Did not dissolve, used as suspension |
| F | acetic acid | 1% | |
| G | N-cyclohexyl-3 aminopropanesulfonic acid (CAPS) buffer (pH ~9) | 10 mM | |

Figure 3A:
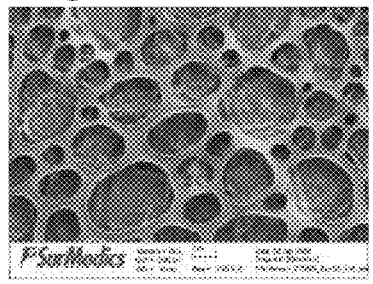
FIGS. 3A-3C are micrographs of air-dried emulsions of silyl ether-modified hydrophobic α(1→4)glucopyranose polymers.
Figure 3B:
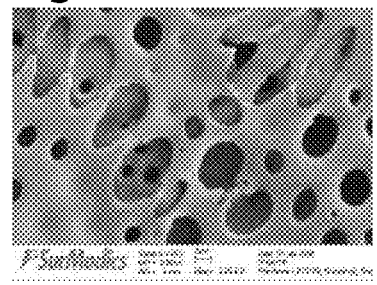
Figure 3C:
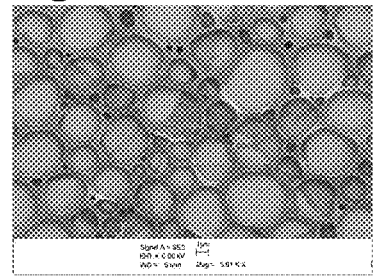

In plastic vials, 5 mL of the MD-Hex-silane solution in dichloromethane was pipetted. 100 μL of each of the aqueous solutions A-G were individually added to the MD-hex-silane solutions and the mixtures were homogenized at 12.4 kRPM for 2 min using a AKI25T homogenizer. Next, a small stir-bar was added to each mixture, which were then stirred for 4 hours at room temperature. The initially suspended dichlorophenylboronic acid immediately dissolved in the MD-Hex-silane solution and similar emulsions were obtained. After 4 hours, 5 μL was taken of each sample, placed on a glass slide, and then air-dried. SEM and light microscope pictures were taken. FIGS. 3A-3C show micrographs of air-dried emulsions of silyl ether-modified hydrophobic α(1→4)glucopyranose polymer. All emulsions were stable for several hours. Typically the emulsion in chloroform creams, however, upon light shaking the emulsion is restored. Overnight, however, some emulsions started to separate, forming bigger water droplets and continuous phases. In samples with boric acid, acetic acid and caps buffer very little remained emulsified. Water, borax and phenylboronic acid still had significant amount of dispersed emulsion, but a drop of continuous aqueous phase of about 5 mm was noticed. The sample containing dichlorophenylboronic acid (DPBA) was still completely emulsified. Results are discussed in Table 3.

TABLE 3

| Emulsion (MD-Hex-silane solution) + | Notes |
|---|---|
| A[2] | Significant amount of dispersed emulsion at 24 hours, but a drop of continuous aqueous phase of about 5 mm noticed |
| B[2] | Significant amount of dispersed emulsion at 24 hours, but a drop of continuous aqueous phase of about 5 mm noticed |
| C[1] | Emulsion was substantially separated after 24 hours |
| D[2] | Significant amount of dispersed emulsion at 24 hours, but a drop of continuous aqueous phase of about 5 mm noticed |

TABLE 3-continued

| Emulsion (MD-Hex-silane solution) + | Notes |
|---|---|
| E[3] | Completely emulsified at 670 hours |
| F[1] | Emulsion was substantially separated after 24 hours |
| G[1] | Emulsion was substantially separated after 24 hours |

[1]least stable
[2]moderately stable
[3]most stable

EXAMPLE 8

MD-Hex Silane Microparticles

A solution of 1 mg/mL MD-Hex-silane (polymer D in Table 1: 56 kDa, DS hex
1.5, DS silane 0.04 (theor.)) was made in dichloromethane. Dichlorophenylboronic acid
(DPBA) in an amount of 10 mg was dissolved in 1 mL in a mixture of dichloromethane/methanol (9:1 ratio). 5 mL aliquots of the MD-Hex-silane solution were pipetted into glass vials and 5 µL of the DPBA solution was added. In a separate vial, 5 µL of the DPBA solution was added to 5 mL of DCM without any polymer.

Increasing amounts of water was pipetted (10 µL-500 µL) into the MD-Hex-silane/DPBA mixtures and dispersed (24 kRPM, 2 min) using AKI 25T homogenizer. The DCM (only) sample immediately separated after emulsification. All other dispersions were observed to cream, but were stable for several weeks leaving them at room temperature.

The emulsified MD-Hex-silane/DPBA mixture was then dried on a glass plate under vacuum for several hours. Chloroform added to the dried samples was able to completely dissolve the material, indicating that if any silanol crosslinking had occurred, the crosslinking was reversible.

Figure 4:
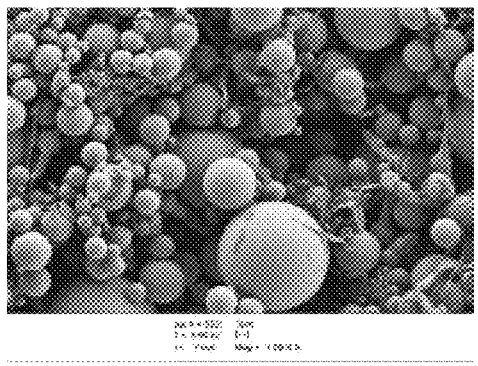
FIG. 4 is a micrograph of microparticles formed using the silyl ether-modified hydrophobic α(1→4)glucopyranose polymer.

Similar to Example 7, an emulsion was formed by addition of 100 µL of DDW to 5 mL of 50 mg/mL MD-Hex-silane with 5 µL of the DPBA solution. A sample of the emulsion was taken (50 µL) and dispersed in 50 mL water (w/o/w emulsion) to create microparticles. Of the resulting suspension a sample was taken and viewed with SEM, and is shown in FIG. 4. The sample fully dissolved upon adding chloroform.

EXAMPLE 9

MD-Hex Silane Microparticles

A solution of MD-Hex-silane (polymer D in Table 1: 56 kDa, DS hex 1.5, DS silane 0.04 (theor.)) at 10% w/w polymer in dichloromethane was prepared. The MD-Hex-silane in an amount of 1 mL was poured into 15 mL of a solution of PVA 2% (w/w) that was saturated with DCM. The mixture was then homogenized for 1 min using a homogenizer (Silverson, 5100 rpm), and then immediately poured in 150 mL of DDW and stirred for 30 min. Particles were isolated by centrifugation (2000 rpm, 30 min.) and lyophilized thoroughly. SEM scanning showed smooth particles. Better yield and particles were obtained with MD-Hex-silane compared to MD-Hex at similar concentrations.

Lysozyme was spray-dried on a Bucchi spray drier (Buchi, Switzerland) using a solution with 70% w/w protein and 30% w/w trehalose. Microparticle formation was repeated using MD-Hex-silane but with the addition of spray-dried lysozyme particles to the polymer solution at 10% or 20% (w/w—solids vs. polymer; 10.8 mg and 23.8 mg respectively).

Figure 5:
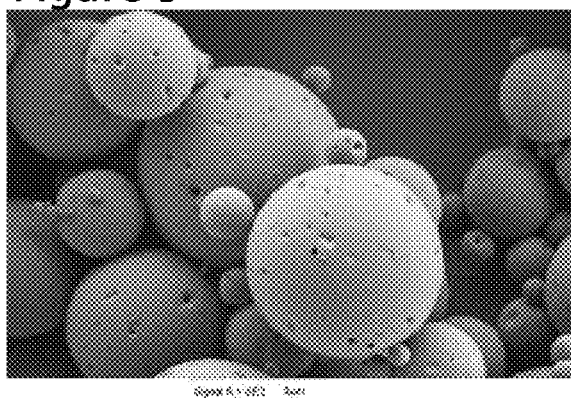
FIG. 5 is a micrograph of microparticles formed using the silyl ether-modified hydrophobic α(1→4)glucopyranose polymer with a lysozyme particle core.

FIG. 5 is a SEM image of microparticles formed according to this method.

What is claimed is:

1. An implantable or injectable biomedical article comprising a polymeric matrix formed from a composition comprising a hydrophobic derivative of a natural biodegradable polysaccharide comprising:

a poly-α(1→4)glucopyranose portion comprising a monomeric unit according formula IIa as follows:

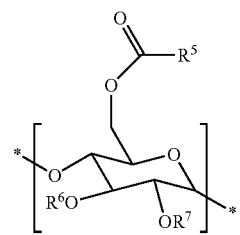

wherein $R^5$ is $-(CH_2)_xCH_3$, and x is an integer in the range of 0-11; and
and wherein $R^6$ and/or $R^7$ is

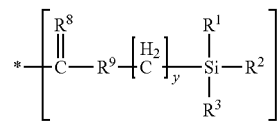

wherein $R^8$ is S or O, $R^9$ is C, O, N, or a covalent bond, y is an integer in the range of 2-8, wherein $R^1$, $R^2$, and $R^3$, are independently selected from $R^4$ or $OR^4$, wherein $R^4$ is a C1-C6-containing hydrocarbon group, with the proviso that at least one of $R^1$, $R^2$, or $R^3$ is $OR^4$, and if $R^6$ or $R^7$ is not as defined above, then $R^6$ or $R^7$ is H.

2. The article of claim 1 wherein $R^1$, $R^2$, and $R^3$ are independently selected from $OR^4$, wherein $R^4$ is selected from the group consisting of $-CH_3$ and $-CH_2CH_3$.

3. The article of claim 1 wherein $R^5$ and

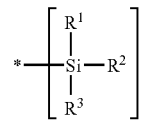

are present at a weight to molar ratio in the range of 50 mgram:1 mmol to 4830 mgram:1 mmol, respectively.

4. The article of claim 1 wherein the poly-α(1→4)glucopyranose portion and

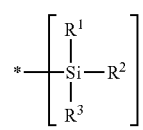

are present at a weight to molar ratio in the range of 77 mgram:1 mmol to 4053 mgram:1mmol, respectively.

5. The article of claim 1 further comprising a monomeric unit according formula IIIa as follows:

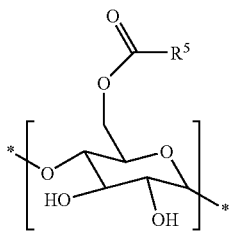

wherein $R^5$ is —$(CH_2)_xCH_3$, and x is an integer in the range of 0-11.

6. An implantable or injectable biomedical article comprising a polymeric matrix formed from a composition comprising a hydrophobic derivative of a natural biodegradable polysaccharide comprising:
a poly-α(1→4) glucopyranose portion comprising a monomeric unit according formula IVa as follows:

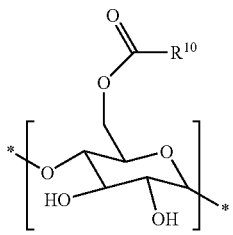

wherein $R^{10}$ is

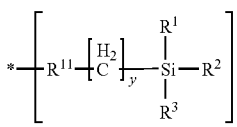

wherein $R^{11}$ is C, O, N, or a covalent bond, y is an integer in the range of 2-8, and wherein $R^1$, $R^2$, and $R^3$ are independently selected from $R^4$ or $OR^4$, wherein $R^4$ is a C1-C6-containing hydrocarbon group, with the proviso that at least one of $R^1$, $R^2$, or $R^3$ is $OR^4$.

7. The article of claim 1 wherein the polysaccharide has a molecular weight in the range of 5 kDa to 1000kDa.

8. A hydrophobic derivative of a natural biodegradable polysaccharide comprising:
a poly-α(1→4)glucopyranose portion;
first groups pendent from the poly-α(1→4)glucopyranose portion having the formula:

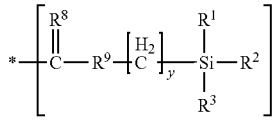

wherein $R^8$ is S or O, $R^9$ is C, O, N, or a covalent bond, y is an integer in the range of 2-8, wherein $R^1$, $R^2$, and $R^3$, are independently selected from $R^4$ or $OR^4$, wherein $R^4$ is a C1-C6-containing hydrocarbon group, with the proviso that at least one of $R^1$, $R^2$, or $R^3$ is $OR^4$, and if $R^6$ or $R^7$ is not as defined above, then $R^6$ or $R^7$ is H; and
second groups pendent from the poly-α(→4)glucopyranose portion, the second groups having the formula

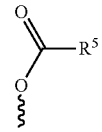

wherein $R^5$ is a $C_2$-$C_{10}$ linear or branched hydrocarbon group, and wherein the ester group in the formula is formed by reaction of a hydroxyl group of the poly-α(1→4)glucopyranose portion.

9. The hydrophobic derivative of claim 8, where $R^5$ is: (a)-$(CH_2)_mCH_3$, and m is an integer in the range of 1 to 5, or (b) selected from the group consisting of ethyl, propyl, isopropyl, n-butyl, isobutyl, and t-butyl, and hexyl.

10. The hydrophobic derivative of claim 8, having a degree of substitution in the range of 0.9 -2.5.

* * * * *